United States Patent [19]
Wilson et al.

[11] Patent Number: 5,196,200
[45] Date of Patent: Mar. 23, 1993

[54] BISABOLENE-CONTAINING COMPOSITION, PROCESS FOR PREPARING SAME, ORGANOLEPTIC USES THEREOF AND USES THEREOF AS INSECT REPELLENT

[75] Inventors: Richard A. Wilson, Westfield; Braja D. Mookherjee, Holmdel; Michael J. Zampino, Roselle Park, all of N.J.; Jerry F. Butler, Gainesville, Fla.

[73] Assignees: International Flavors & Fragrances Inc., New York, N.Y.; The University of Florida, Gainesville, Fla.

[21] Appl. No.: 847,342

[22] Filed: Mar. 6, 1993

Related U.S. Application Data

[63] Continuation of Ser. No. 691,635, Apr. 25, 1991, abandoned.

[51] Int. Cl.$^5$ .................. A01N 25/34; A01N 27/00
[52] U.S. Cl. .................. 424/411; 424/405; 424/DIG. 10; 514/763; 514/919
[58] Field of Search ............... 424/405, 406; 514/763

[56] References Cited

U.S. PATENT DOCUMENTS

| | | | |
|---|---|---|---|
| 3,988,432 | 10/1976 | Steltenkamp | 424/49 |
| 4,376,068 | 3/1983 | Mookherjee et al. | 252/522 R |
| 4,449,987 | 5/1984 | Lindauer et al. | 44/7.5 |
| 4,735,803 | 4/1988 | Katz et al. | 424/195.1 |
| 4,853,413 | 8/1989 | Katz et al. | 514/526 |
| 5,089,469 | 2/1993 | Zampino et al. | 512/22 |

OTHER PUBLICATIONS

Arctander, "Perfume and Flavor Chemicals (Aroma Chemicals)", vol. I, published by the author, 1969, Mongraph 348, Bisabolene.

Beroza and Green, "Materials Tested as Insect Attractants", Agriculture Handbook No. 239, Published by the Agricultural Research Service, U.S. Department of Agriculture, Issued Jun., 1963, Table II, Item Nos. 24 and 55, 3-(i-butenyl)-2,4,4—trimethyl-cyclohexene (Item 24) and beta-phellandrene, Items 55 and 56).

Ruzicka and Capato, Helv. Chem. Acta. 8, 259 (1925).

*Primary Examiner*—Thurman K. Page
*Assistant Examiner*—Neil Levy
*Attorney, Agent, or Firm*—Arthur L. Liberman

[57] ABSTRACT

Described are isomeric mixtures of bisabolene prepared by dehydrating nerolidol using citric acid or phosphoric acid and then distilling the resulting product at particular temperature ranges and particular pressure ranges in order to prepare a composition of matter useful for augmenting or enhancing natural, dry, floral, opoponax aromas with floral, freesia, fruity, citrus, bergamot, mango and opoponax topnotes in perfume compositions, colognes and perfumed articles (e.g., solid or liquid anionic, cationic, nonionic or zwitterionic detergents, fabric softener composiitions, drier-added fabrics softener articles, cosmetic powders and the like; and useful for repelling specific species of insects, namely, house flies *Musca domestica* L. (Diptera Muscidae)) and the species of mosquitoes, *Aedes aegypti*.

4 Claims, 8 Drawing Sheets

GLC PROFILE FOR EXAMPLE II.

GLC PROFILE FOR EXAMPLE I.

GLC PROFILE FOR EXAMPLE II.

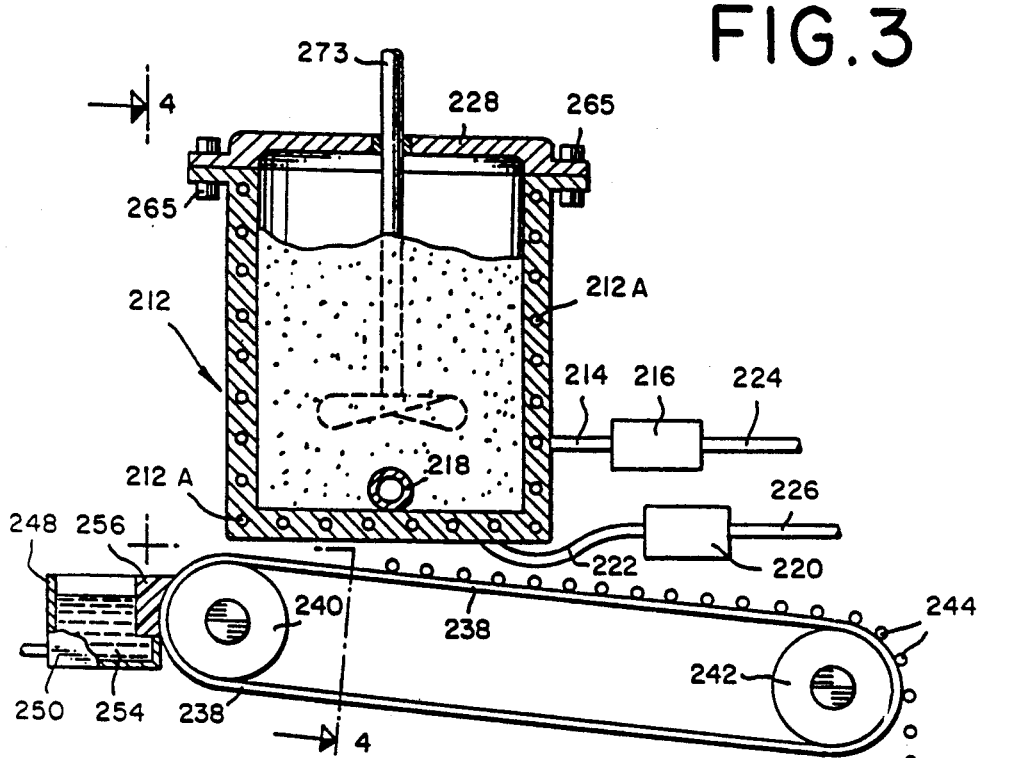

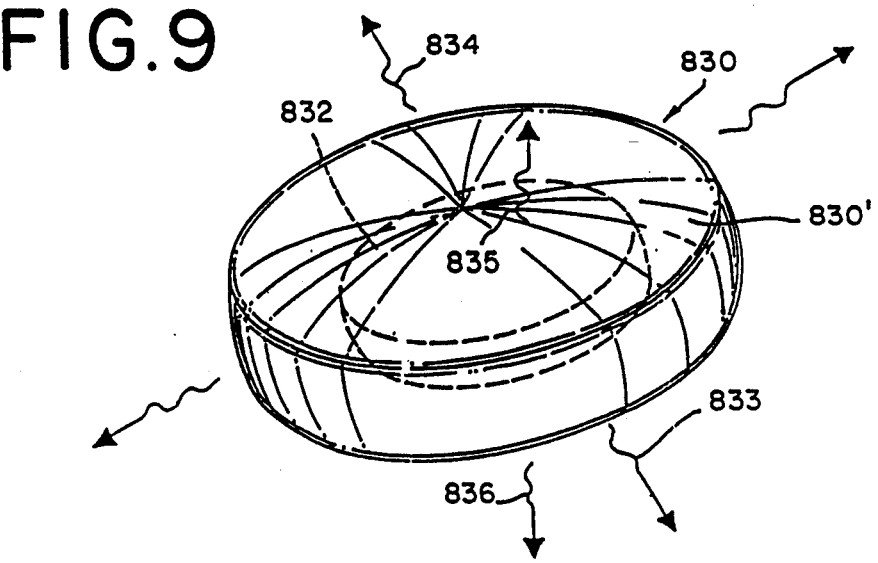
FIG.9
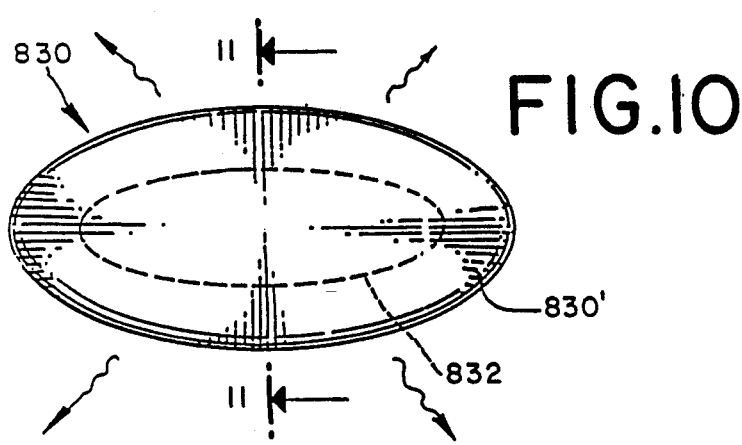
FIG.10
FIG.11
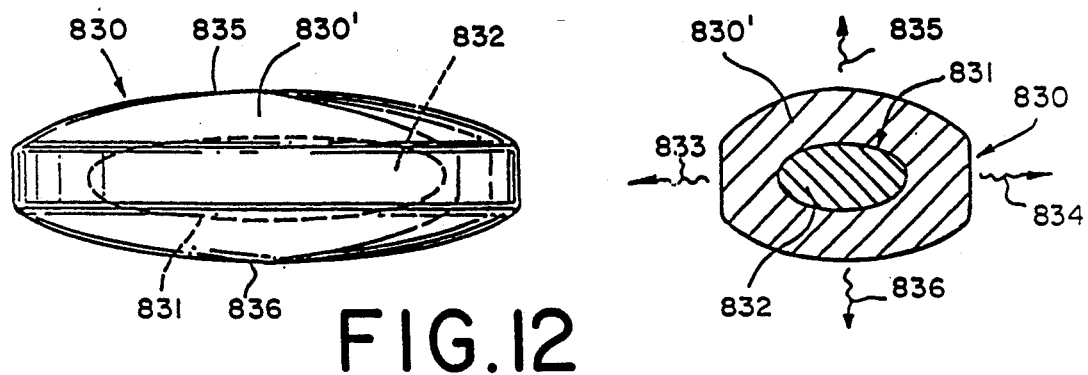
FIG.12

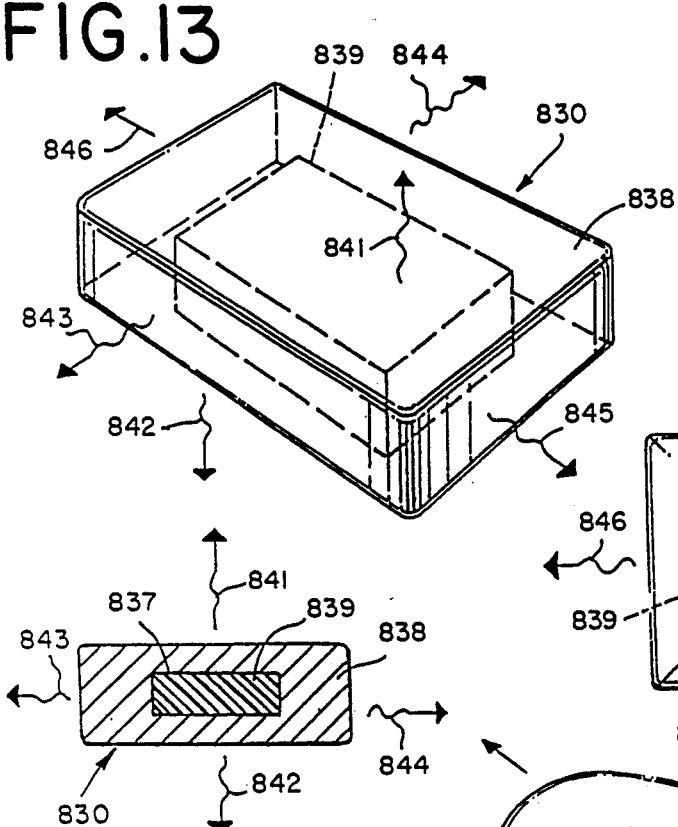
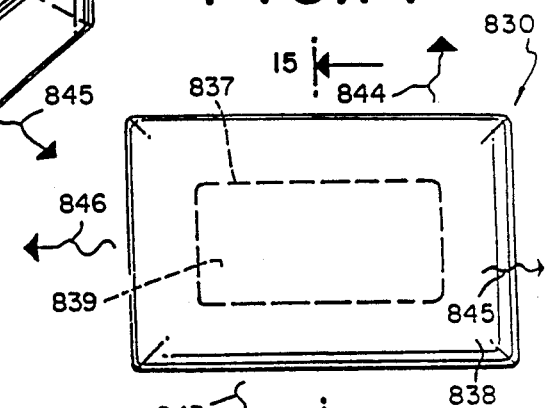
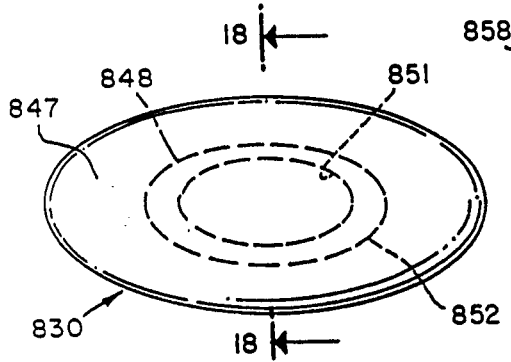
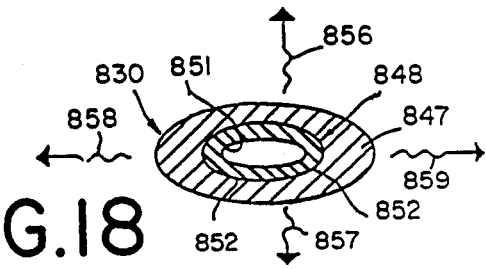

BISABOLENE-CONTAINING COMPOSITION, PROCESS FOR PREPARING SAME, ORGANOLEPTIC USES THEREOF AND USES THEREOF AS INSECT REPELLENT

This is a continuation of application Ser. No. 691,635, filed Apr. 25, 1991, now abandoned.

BACKGROUND OF THE INVENTION

The present invention relates to bisabolene isomer mixtures containing, but not limited to, compounds defined according to the structure:

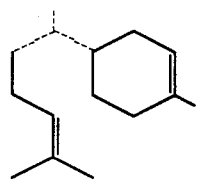

including the compounds having the structures:

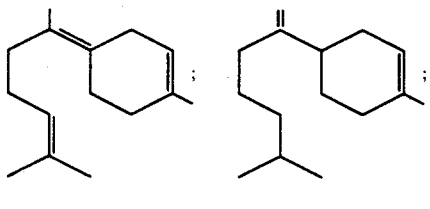

and

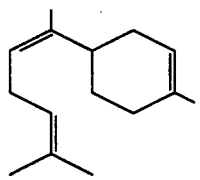

and uses of such mixtures in augmenting or enhancing the aroma of perfume compositions, perfumed articles and colognes; as well as uses thereof in repelling insects including *Musca domestica* L.(Diptera Muscidae) and *Aedes aegypti*.

The compositions of our invention are prepared by dehydrating nerolidol using citric acid or phosphoric acid dehydrating agents. Nerolidol isomers are defined according to the structure:

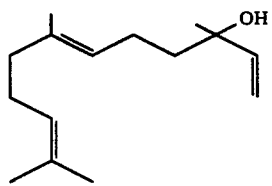

and include cis and trans isomers thereof shown by the structures:

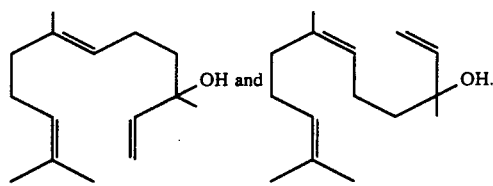

There has been considerable work performed relating to substances which can be used to impart (modify, augment or enhance) fragrances to (or in) various consumable materials. The substances are used to diminish the use of natural materials, some of which may be in short supply and to provide more uniform properties in the finished product.

Natural, dry, floral, opoponax aromas with floral, freesia, fruity, citrus, bergamot, mango and opoponax topnotes are particularly desirable in several types of perfume compositions, perfumed articles and colognes, including "ginger" perfumes.

Arctander "Perfume and Flavor Chemicals (Aroma Chemicals)", Volume I, at monograph 348 indicates that gamma bisabolene having the structure:

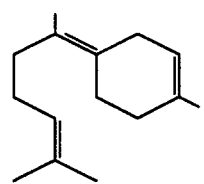

has a pleasant, warm, sweet spicy, balsamic aroma inevitably reminding the perfumer of opoponax and "oriental" fragrance types. Arctander further states that gamma bisabolene finds good use in artificial oils of bergamot, myrrh, lemon and the like. Arctander further states that it may be produced from nerolidol "by dehydration".

Furthermore, Ruzicka and Capato, Helv. Chim. Acta 8, 259(1925) indicates that nerolidol having the structure:

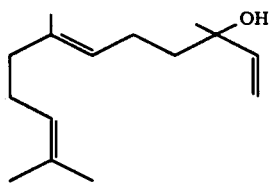

can be dehydrated to using formic acid to produce alpha bisabolene having the structure:

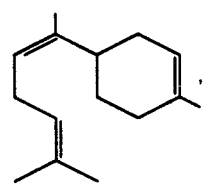

beta bisabolene having the structure:

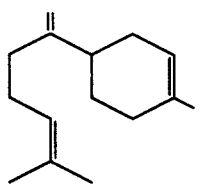

and gamma bisabolene having the structure:

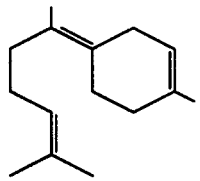

as well as bisabolol having the structure:

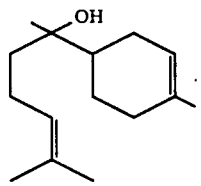

However, Ruzicka and Capato and for that matter, any other relevant prior art do not disclose the use of citric acid or phosphoric acid to dehydrate nerolidol or natural materials containing nerolidol in large quantities such as Cabreuva oil to produce the novel composition of matter of our invention which has unexpected, unobvious and advantageous properties not only insofar as its organoleptic character is concerned but also regarding its character as a semio chemical; that is, in order to repel the insects, Musca domestica L.(Diptera Muscidae) as well as Aedes aegypti. Reference to Cabreuva oil as containing a large amount of nerolidol is set forth at columns 108 and 109 of "Perfume and Flavor Materials of Natural Origin", Arctander, 1960.

Arctander "Perfume and Flavor Chemicals (Aroma Chemicals)", at Monograph 1378, discloses "Farnesal", 2,6,10-trimethyl-2,6,10-dodecatrien-12-al to have a very mild, sweet oily, slightly woody, tenacious odor. On the other hand, Arctander also describes, at Monograph 1379, Farnesene, 2,6,10-trimethyl-2,6,9,11-dodecatetraene defined according to the structure:

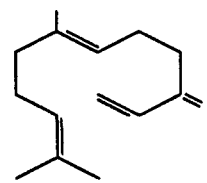

to have a very mild, sweet and warm, rather nondescript odor of good tenacity. Arctander further states that apart from some possible use in the reconstruction of certain essential oils, there is to the author's knowledge, very little, if any, use for this sesquiterpene in perfumery as such. Arctander further states that Farnesene having the structure:

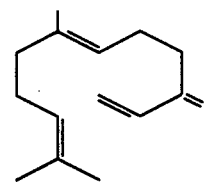

is produced by dehydration of Farnesol by heat with a potassium dehydrating agent or from Nerolidol by heat with acetic anhydride.

Brieger, et al, J. Org. Chem., Volume 34, No. 12, December, 1969, in their paper "The Synthesis of trans,trans-alpha Farnesene" discloses dehydration of nerolidol using bisulfate at 170° C. to yield a number of Farnesene isomers according to the reaction:

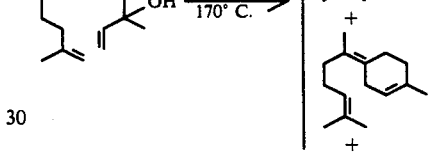
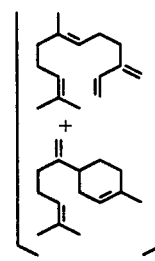

Brieger, et al also discloses the dehydration of Farnesol using potassium bisulfate at 170° C. as follows:

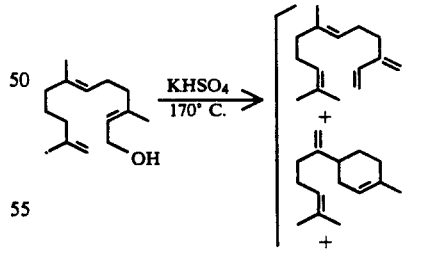
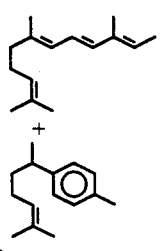

Brieger also teaches the dehydration of Farnesol using potassium hydroxide at 210° C. to yield certain isomers according to the following reaction:

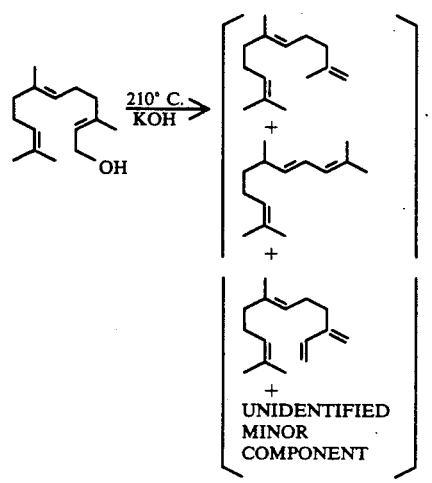

Anet, Aust. J. Chem., 1970, 23, 2101–8, in a paper entitled "Synethesis of (E,Z)-alpha-, (Z,Z)-alpha-, and (Z)-β-Faranesene" discloses the dehydration of (E)-nerolidol having the structure:

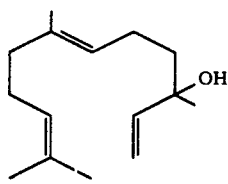

in the presence of such dehydrating agents as phosphoryl chloride in pysridene to yield the compounds having the structures:

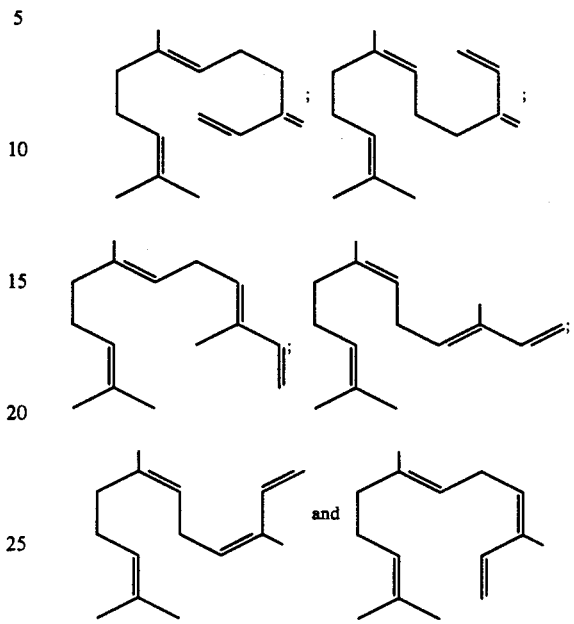

according to the reaction:

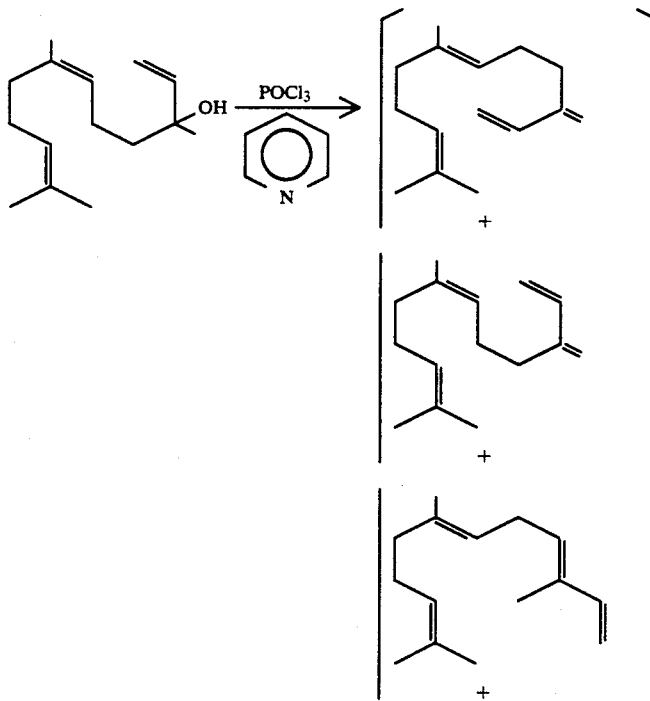

-continued

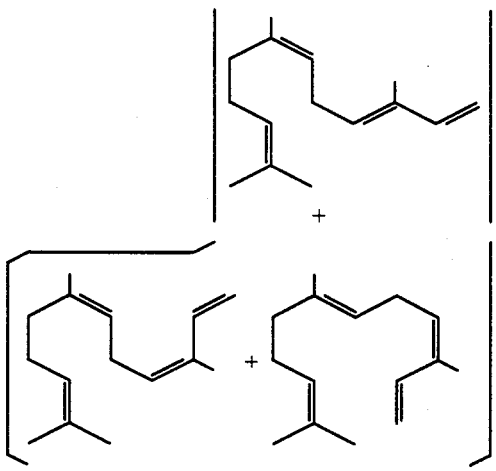

In a paper by Hattori, et al entitled "Chemical Composition of the Absolute from Gardenia Flower" and in another paper by Tsuneya, et al entitled "GC-MS Analysis of Gardenia Flower Volatiles", it is disclosed that alpha-farnesene is existent in gardenia flower absolute. The Hattori, et al and Tsuneya, et al papers are published in the "VII International Congress of Essential Oils; Japan Flavor and Fragrance Manufacturers' Association, Tokyo (1979) at pages 451 and 454, respectively (papers 128 and 129, respectively).

Beroza, "Materials Tested As Insect Attractants", Agriculture Handbook No. 239, Agricultural Research Service, United States Department of Agriculture, June, 1963, at Table 2, discloses the use of certain hydrocarbons as insect attractants. Thus, Item No. 24 is 3-(1-butenyl)-2,4,4-trimethyl cyclohexene and is shown to be an attractant for the Oriental fruit fly, the Mediterranean fruit fly and the Mexican fruit fly as well as the Gypsy Moth and the Boll Weevil at levels of "1" on a scale of 1-3 and at a level of "2" for the Pink Bollworm. This compound has the structure:

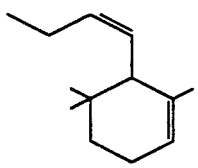

Beta phellandrene is also shown by Beroza, et al to be an attractant for the Oriental fruit fly at a level of "3" on a scale of 1-3 and an attractant for the Mediterranean fruit fly at a level of "1" on a scale of 1-3. Beta phellandrene is indicated as Item No. 56, in Table 2 of the Beroza reference. Beta phellandrene has the structure:

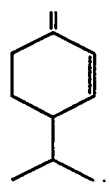

No structures remotely resembling the structure of any of the bisabolene isomers of our invention is shown to be a repellent or for that matter is shown to have any activity towards insects in the prior art. Furthermore, nothing in the prior art indicates the unexpected, unobvious and advantageous perfumery property of the composition of matter defined according to our invention. Accordingly, not only does the composition of matter defined according to our invention have valuable organoleptic properties from a perfumery standpoint but said composition also has valuable properties insofar as its insect repellency is concerned with regard to *Musca Domestica* L.(Diptera Muscidae) and *Aedes aegypti*. Interestingly, the composition of matter of our invention in addition has properties as a flavorant also.

SUMMARY OF THE INVENTION

It has now been discovered that novel solid and liquid perfume compositions, colognes and perfumed articles having natural, dry, floral, opoponax aromas, with floral, freesia, fruity, citrus, bergamot, mango and opoponax topnotes may be provided by an isomeric mixture of bisabolene derivatives (containing a number of other compounds) defined according to the processes for producing same by the dehydration of various isomeric mixtures of E (trans) and Z (cis) nerolidol having the structures:

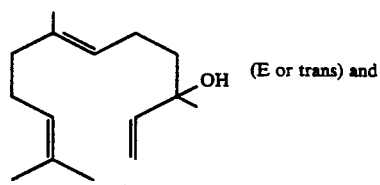

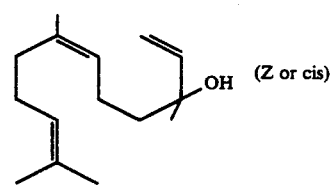

using citric acid or phosphoric acid dehydration catalyst over a particular temperature and pressure range for a given reaction time range.

The reaction to produce the products of our invention may be set forth as follows:

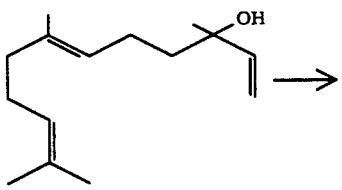

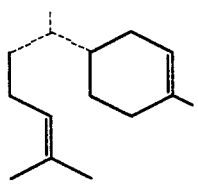

wherein the catalyst used may be citric acid or phosphoric acid.

The nerolidol isomers used may be in the form of a natural isomeric mixture, e.g., Cabreuva oil or they may be mixtures synthetically produced of "cis" and "trans" isomers. The ratio of E (trans) or Z (cis) nerolidol isomers having the structures:

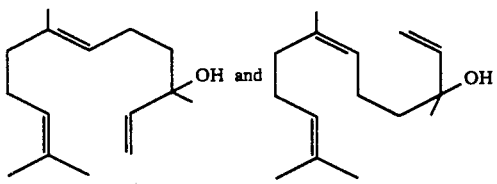

used in the reaction mass may vary from 0:100 E isomer:Z isomer up to 100:0 E isomer:Z isomer. Although the isomer mixture is substantially the same whether using phosphoric acid or citric acid as a catalyst, the specific reaction conditions using the two catalysts vary from another.

When using citric acid as well as phosphoric acid as a catalyst, the temperature range for the reaction is preferably between 155° C and 175° C. When using the citric acid catalyst or the phosphoric acid, it is necessary to utilize a solvent for the reaction mass which will:
(a) be inert to the reaction; and
(b) have a boiling point at the reaction pressure which will be conveniently greater than the reaction temperature so that the solvent will not volatilize from the reaction mass.

Thus, when using citric acid as a catalyst or phosphoric acid as a catalyst at a temperature in the range of 155°-175° C., it is most preferable to use a heavy hydrocarbon mineral oil, for example, PRIMOL ® (manufactured by the Exxon Corporation of Linden, N.J.). Other inert solvents such as toluene and xylene may be used but, when using toluene, the pressure over the reaction mass must be such that the reaction mass will reflux in the range of 155°-175° C. Thus, when using a toluene or xylene solvent, a positive nitrogen pressure over the reaction mass is necessary in order to maintain the reaction temperature at 155°-175° C.

Thus, when using the citric acid catalyst or the phosphoric acid catalyst, not only is the temperature range important, e.g., 155°-175° C., but the pressure range is equally as important; from 1 up to 200 atmospheres pressure. Using pressures greater than 1 atmosphere necessitates the use of high pressure equipment and appropriate safety precautions.

Whether using a phosphoric acid catalyst or a citric acid catalyst, it is preferable to remove the water of reaction as it is formed. Thus, during refluxing, a phase separation column is necessarily utilized whereby the water of reaction is removed during the course of the reaction. For example, a Bidwell water trap is the type of trap used in the laboratory when removing the water of reaction.

The time of reaction is necessarily dictated by the rate at which the nerolidol reaction mixture or Cabreuva oil is added to the catalyst/solvent mixture. It is preferable to add the nerolidol or Cabreuva oil to the catalyst/solvent mixture over a period of between 1 and 5 hours.

Whether using a phosphoric acid catalyst or a citric acid catalyst, the ratio of catalyst to nerolidol may vary from 1:1000 (weight/weight) up to 1:5 with a preferred ratio of 1:10 when using a citric acid catalyst or a phosphoric acid catalyst. The concentration of catalyst in the reaction mixture may vary from about 1:50 to about 1:5 with a preferred concentration of catalyst when using citric acid of 1:30 and a preferred concentration of catalyst when using phosphoric acid of 1:20.

The ratio of solvent:nerolidol isomer mixture varies depending upon the particular solvent used and the desired catalyst concentration. Thus, when using a heavy hydrocarbon inert mineral oil and a citric acid catalyst, the ratio of solvent:nerolidol isomer mixture may vary between 4:1 and 1:4 with a preferred ratio of 2:1. When using a phosphoric acid catalyst, the ratio of solvent:nerolidol isomer mixture may vary from 2:1 up to 1:2 with a preferred ratio being about 1:1. When using a toluene solvent or a xylene solvent the preferred weight/weight ratio may vary from 1:2 up to 2:1 with a most preferred weight ratio of nerolidol isomer mixture:solvent being 1:1.

The product produced according to the process of our invention contains other materials besides the alpha bisabolene, beta bisabolene and gamma bisabolene, for example, trans-beta-farnesene having the structure:

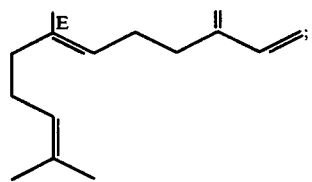

gamma curcumene having the structure:

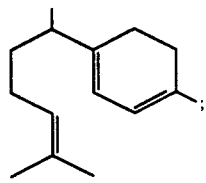

epizonarene having the structure:

trans,trans-alpha farnesene having the structure:

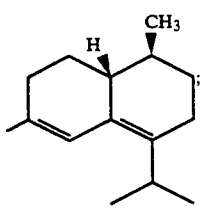

allofarnesene having the structure:

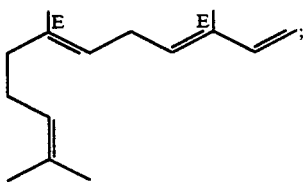

a zonarene isomer having the structure:

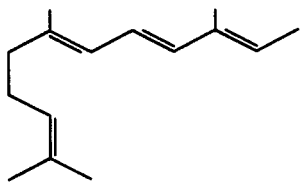

and another hydrocarbon having the structure:

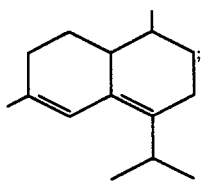

Nevertheless, the bisabolene isomers defined according to the generic structure:

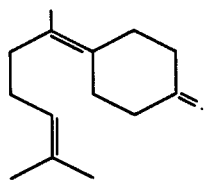

wherein one of the dashed lines is a carbon-carbon double bond and each of the other of the dashed lines represent carbon-carbon single bonds in each of the compounds of the mixture is the predominant material. This is only true in the case where the citric acid or phosphoric acid catalysts are used. When other catalysts are used, the amount of bisabolene isomers is in the minority.

Thus, when using para toluene sulfonic acid as a catalyst in PRIMOL ® at 165° C., the ratio of bisabolene isomers:farnesene isomers is 15.2:47.4.

When FILTROL ® 25 (an acid ion exchange resin) is used, mostly polymer is obtained.

When DOWEX ® 50 (an acid ion exchange resin) is used, analysis shows 20% of an unknown low molecular weight; 14% of unreacted nerolidol and the remainder of the mixture various bisabolenes and farnesenes.

When sulfuric acid is used, no bisabolene or farnesene is produced using the foregoing conditions.

The product-by-process of our invention, the bisabolene isomer mixture and one or more auxiliary perfume ingredients including, for example, alcohols, aldehydes, ketones, nitriles, esters, cyclic esters (lactones), dialkyl ethers, alkyl alkenyl ethers, thioethers, thiols, carboxylic acids and hydrocarbons other than the bisabolene isomeric mixture of our invention and natural essential oils may be admixed so that the combined odors of the individual components produce a pleasant and desired fragrance, particularly and preferably in ginger fragrances. Such perfume compositions usually contain (a) the main note or the "bouquet" or foundation stone of the composition; (b) modifiers which round off and accompany the main notes; (c) fixatives which include odorous substances which lend a particular note to the perfume throughout all stages of evaporation and substances which retard evaportaion; and (d) top notes which are usually low-boiling, fresh-smelling materials.

In perfume compositions, it is the individual components which contribute to their particular olfactory characteris.ics, however, the overall sensory effect of the perfume composition will be at least the sum total of the effects of each of the ingredients. Thus, the bisabolene isomer mixture produced according to the process of our invention can be used to alter, modify or enhance the aroma characteristics of a perfume composition, for example, by utilizing or moderating the olfactory reaction contributed by another ingredient in the composition.

The amount of bisabolene isomer mixture of our invention which will be effective in perfume compositions, as well as in perfumed articles and colognes depends on many factors, including the other ingredients, their amounts and the effects which are desired. It has been found that perfume compositions containing as little as 0.01% of the bisabolene isomer mixture or even less, (e.g., 0.005%) can be used to impart a very natural, dry, floral, opoponax aroma, with floral, freesia, fruity, citrus, bergamot, mango and opoponax topnotes to soaps, cosmetics and other products. The amount employed can range up to 70% of the fragrance components and will depend on considerations of cost, nature of the end product, the effect desired on the finished product and the particular fragrance sought.

The bisabolene isomer mixture produced according to the process of our invention is useful (taken alone or together with other ingredients in perfume compositions) as (an) olfactory component(s) in detergents and soaps, space odorants and deodorants, perfumes, colognes, toilet waters, bath preparations such as lacquers, brilliantines, pomades and shampoos; cosmetic preparations such as creams, deodorants, hand lotions and sun screens; powders such as talcs, dusting powders, face

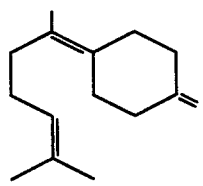

powders, and perfumed article compositions of matter such as perfumed polypropylene, polyethylene and polyurethanes, particularly long-lasting mixtures of, for example, encapsulated perfumes suspended in free perfume compositions and the like. When used as (an) olfactory component(s), as little as 0.1% of the bisabolene isomer mixture of our invention will suffice to impart an intense, natural, dry, floral, opoponax aroma with floral, freesia, fruity, citrus, bergamot, mango and opoponax topnotes to ginger formulations. Generally, no more than 3% of the bisabolene isomer mixture of our invention based on the ultimate end product is required in the perfume composition.

In addition, the perfume composition or fragrance composition of our invention can contain a vehicle or carrier for the bisabolene isomer mixture. The vehicle can be a liquid such as a non-toxic alcohol, (e.g., ethyl alcohol), a non-toxic glycol (e.g., propylene glycol or 1,2-butylene glycol or sorbitol) or the like. The carrier can also be an absorbent solid such as a gum (e.g., gum arabic, xanthan gum or the like) or components for encapsulating the composition (such as gelatin or ethyl cellulose) as by coacervation.

When used as a component of a perfumed article such as a perfumed plastic or solid or liquid anionic, cationic, nonionic or zwitterionic detergent or drier-added fabric softener article or a fabric softener composition or a shampoo or a soap, the range of bisabolene isomer composition usable varies from 0.005% up to about 5% by weight of the perfumed article. The lower end of this range, e.g., 0.005% up to 0.1% of the bisabolene isomer mixture of our invention is most preferred when using it in a drier-added fabric softener article or fabric softener composition in view of the need for "non-perfumey" but pleasant head space aroma above the batch of clothes being dried using a drier-added fabric softener article or fabric softener composition in a standard automatically operated tumbler dryer.

When the bisabolene isomer composition of our invention produced according to the process of our invention is used as a food flavor adjuvant, the nature of the coingredients included with the bisabolene isomer composition used in formulating the product composition will also serve to alter, modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble chewable plastic gum base such as chicle, or substitutes therefor, including jelutong, guttakay rubber or certain comesible natural or synthetic resins or waxes. Incorporated with the gum base in admixture therewith may be plasticizers or softening agents, e.g., glycerine, and a flavoring composition which incorporates the bisabolene isomer composition of our invention and, in addition, sweetening agents which may be sugars, including sucrose or dextrose and/or artificial sweeteners such as cyclamates or saccharine. Other optional ingredients may also be present.

Substances for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may, in general, be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl galla'e and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids, carbohydrates; starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like, colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nitrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanol, cortonal, diacetyl, 2-methyl butanol, $\beta,\beta$-dimethyl acrolein, methyl-n-amyl ketone, n-hexanal, 2-hexenal, isopentanal, hydrocinnanic aldehyde, cis-3-hexenal, 2-heptenal nonyl aldehyde, 4-(p-hydroxyphenyl)-2-butanone, alpha-ionone, beta-ionone, methyl-3-butanone, benzaldehyde, $\beta$-damascone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, n-hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines, such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones, such as gamma-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the bisabolene isomer composition of our invention by not covering or spoiling the organoleptic properties (aroma and/or taste) thereof; (ii) be non-reactive with the bisabolene isomer composition of our invention and (iii) be capable of providing an environment in which the bisabolene isomer composition of our invention can be dispersed or admixed to provide a homogeneous medium. In addition, selection of one or more flavor adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste or chewing tobacco to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of bisabolene isomer composition thereof of our invention employed in a particular instance can vary over a relatively wide range, depending upon the desired organoleptic effects to be achieved. Thus, correspondingly greater amounts would be necessary in those instances wherein the ultimate food composition to be flavored (e.g., a "raisin-rum cake") is relatively bland to the taste, whereas relatively minor quantities may suffice for purposes of enhancing the composition merely deficient in natural flavor or aroma, (e.g., when actual raisins and rum are present in the foodstuff such as the cake). The primary requirement is that the amount selected by effective, i.e., sufficient to alter, modify or enhance the organoleptic characteristics of the parent composition, whether foodstuff per se, chewing gum per se, medicinal product per se, toothpaste per se, chewing tobacco per se or flavoring composition.

The use of insufficient quantities of bisabolene isomer composition of our invention will, of course, substantially vitiate any possibility of obtaining the desired results while excess quantities prove needlessly costly and in extreme cases, may disrupt the flavor aroma balance, thus proving self-defeating. Accordingly, the terminology "effective amount" and "sufficient amount" is to be accorded a significance in the content of the present invention consistent with the obtention of desired flavoring effects.

Thus, and with respect to ultimate food compositions, chewing gum compositions, medicinal product compositions, chewing tobacco compositions and toothpaste compositions, it is found that quantities of bisabolene isomer composition of our invention ranging from a small but effective amount, e.g., about 0.05 parts per million up to about 150 parts per million based on total food composition or chewing gum composition, or medicinal product composition or tobacco composition or chewing tobacco composition are suitable. Concentrations in excess of the maximum quantity stated are not normally recommended since they fail to provide commensurate enhancement of organoleptic properties. In those instances where the bisabolene isomer composition of our invention is added to the foodstuff as an integral component of a flavoring composition, it is, of course, essential that the total quantity of flavoring composition employed be sufficient to yield an effective concentration of the bisabolene isomer composition of our invention in the foodstuff product.

Food flavoring compositions containing one or more of the compounds prepared in accordance with the present invention preferably contain the bisabolene isomer composition in concentrations ranging from about 0.02% up to about 15% by weight of the total weight of said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the bisabolene isomer composition of our invention prepared in accordance with our invention with, for example, gum arabic, gum tragacanth, xanthan gum, carrageenan and the like, and thereafter spray-drying the resultant mixture whereby to obtain the particulate solid product. Pre-prepared flavor mixes in powder form, e.g., a fruit flavored or rum flavored powder mix are obtained by mixing the dried solid components, e.g., starch, sugar and the like and the bisabolene isomer composition of our invention in a dry blender until the requisite degree of uniformity is achieved.

It is presently preferred to combine the bisabolene isomer composition of our invention with at least one of the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha- ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethol;
2,3-Dimethyl pyrazine;
2-Ethyl-3-methyl pyrazine;
3-Phenyl-4-pentenal;
2-Phenyl-2-hexenal;
2-Phenyl-2-pentenal
3-Phenyl-4-pentenal diethyl acetal;
$\beta$-Damascone (1-crotonyl-2,6,6-trimethylcyclohex-1-ene);
$\beta$-Damascenone (1-crotonyl-2,6,6-trimethylcyclohexa-1,3-diene);
Beta-cyclohomocitral (2,6,6-trimethylcyclohex-1-ene-carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene);
2-(4-Hydoxy-4-methylpentyl) norbornadiene rum essence 3-hydroxy butyric acid;
2-Hydroxy butyric acid;
n-Methyl anthranilate cyclotene;
Ethyl cyclotene;
n-Propyl cyclotene; and
Gin berry essence.

Furthermore, the bisabolene composition of our invention prepared in accordance with the processes of our invention are capable of supplying and/or potentiating certain flavor and aroma notes usually lacking in many smoking tobacco flavors and substitute tobacco flavors provided herein.

As used herein in regard to smoking tobacco flavors, the terms "alter" and "modify" in their various forms mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired oriental, and Turkish tobacco-like notes on smoking and prior to smoking in the main stream and in the side stream are created or enhanced and may be readily controlled and maintained at the desired uniform level regardless of variations in the tobacco components of the blend.

Our invention further provides improved smoking tobacco additives and methods whereby various oriental and Turkish tobacco notes prior to smoking and on smoking are imparted (in the main stream and in the side stream) to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing a bisabolene composition of our invention prepared in accordance with the processes of our invention.

In addition to a bisabolene composition of our invention prepared in accordance with the processes of our invention, other flavoring and aroma additives may be added to the smoking tobacco materials or substitute therefor either separately or in admixture with a bisabolene composition of our invention as follows:

(I) SYNTHETIC MATERIAL

Beta-ethyl-cinnamaldehyde;
Beta-cyclohomocitral;
Eugenol;
Dipentene;
$\beta$-Damascenone;
$\beta$-Damascone;

Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;;
Dodecahydro-3a,6,6,9a-tetramethylnaphtho[2,1b]furan;
4-Hydroxy hexanoic acid, gamma lactone; and
Polyisoprenoid hydrocarbons defined in Example V of U.S. Pat. No. 3,589,372 issued on Jun. 29, 1971.

(II) NATURAL OILS

Celery seed oil;
Coffee extract;
Bergamot Oil;
Cocoa extract;
Nutmeg oil; and
Origanum oil.

An aroma and flavoring concentrate containing a bisabolene composition of our invention and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with the taste but insofar as the enhancement or the imparting of natural and/or oriental notes, we have found that satisfactory results are obtained if the proportion by weight of the sum total of a bisabolene composition of our invention to smoking tobacco material is between 250 ppm and 1,500 ppm (0.025%–0.15%) of the active ingredients to the smoking tobacco material. We have further found that satisfactory results are obtained if the proportion by weight of the sum total of a bisabolene composition of our invention is between 2,500 and 15,000 ppm (0.25%–1.50%).

Any convenient method for incorporating a bisabolene composition prepared in accordance with the process of our invention in the tobacco product may be employed. Thus, a bisabolene composition of our invention taken alone or along with other flavoring additives may be dissolved in a suitable solvent such as ethanol, pentane, diethyl ether and/or other organic solvents and the resulting solution may be either sprayed on the cured, cased and blended tobacco material or the tobacco material may be dipped into such solution. Under certain circumstances a solution containing a bisabolene composition of our invention prepared in accordance with the process of our invention taken alone or taken further together with other flavoring additives as set forth above may be applied by means of a suitable applicator such as a brush or roller on the paper or leaf wrapper for the smoking product, it may be applied to the filter by either spraying, or dipping, or coating.

Furthermore, it will be apparent that only a portion of the smoking tobacco or substitute therefor need be treated and the thus treated tobacco may be blended with other tobaccos before the ultimate tobacco product is formed. In such cases, the tobacco treated may have a bisabolene composition of our invention in excess of the amount or concentrations above indicated so that when blended with other tobaccos, the final product will have the percentage within the indicated range.

In accordance with one specific example of our invention, an aged, cured and shredded domestic Burley tobacco is sprayed with a 20% ethyl alcohol solution of a mixture of bisabolene derivatives prepared according to Example I, infra, in an amount to provide a tobacco composition containing 800 ppm by weight of the bisabolene mixture prepared according to Example I, infra.

Thereafter, the alcohol is removed by evaporation and the tobacco is manufactured into cigarettes by the usual techniques. The cigarette, when treated as indicated, has a desired and pleasing aroma prior to smoking which can be described as oriental-like and Turkish and on smoking in the main stream and the side stream as sweet oriental-like and Turkish tobacco-like with faint but aesthetically pleasing fruity undertones.

While our invention is particularly useful in the manufacture of smoking tobacco such as cigarette tobacco, cigar tobacco and pipe tobacco, other smoking tobacco products formed from sheeted tobacco dust or fines may also be used. Likewise a bisabolene composition of our invention can be incorporated with materials such as filter tip materials, seam paste, packaging materials and the like which are used along with tobacco to form a product adapted for smoking. Furthermore, a bisabolene composition of our invention can be added to certain tobacco substitutes of natrual or synthetic nature (e.g., dried lettuce leaves) and, accordingly, by the term "tobacco" is used throughout this specification is meant any composition intended for human consumption by smoking or otherwise, whether composed of tobacco plant parts or substitute materials or both.

It will thus be apparent that the bisabolene isomer mixtures of our invention can be utilized to augment, alter, modify, or enhance sensory properties particularly organoleptic properties of a wide variety of consumable materials.

Our invention is also directed to a method for repelling at least one of the insect species:
(a) *Musca domestica* L.(Diptera Muscidae); and
(b) *Aedes aegypti*
for a finite period of time from a three dimensional space comprising the step of exposing said three dimensional space to a:
(a) *Musca domestica* L.(Diptera Muscidae); and/or
(b) *Aedes aegypti*
repelling concentration and quantity of a composition of matter which is the bisabolene composition of our invention produced according to the process of our invention.

Our invention is also directed to an insect repelling soap which can repel any of the species of insects set forth above comprising a soap base and in intimate contact therewith at least one insect repellent composition of matter which is a bisabolene-containing composition produced by the process of our invention.

Another aspect of our invention relates to the formation of the insect repelling articles, that is, articles containing the bisabolene composition of our invention useful for the repelling of the insect species:
(a) *Musca domestica* L.(Diptera Muscidae); and/or
(b) *Aedes aegypti*
in combination with compatible polymers, e.g., high density polyethylene or low density polyethylene. Thus, one aspect of our invention provides a process for forming semiochemical-containing polymeric particles such as foam polymeric pellets which include a relatively high concentration of a bisabolene composition of our invention.

Thus, one aspect of our invention relates to the formation of semiochemical polymeric pellets by means of introduction into a single screw or twin screw extruder of, in series, thermoplastic polymer followed by the semiochemical which is compatible with the thermoplastic polymer, in turn (optionally) followed by introduction of a gaseous blowing agent or blowing agent which will produce a gas which is inert to the polymer and to the bisabolene isomer containing composition semiochemical previously introduced into the extruder.

The advantages of using a foamed polymeric particle are multiple, to wit: improved handling, greater retention of the semiochemical, a bisabolene isomer containing composition of our invention, when not in use; greater length of time during which release of the semiochemical from the polymer is at "steady state" or "zero order".

The nature of the extruder utilized in the process of our invention to form the polymeric semiochemical-containing polymer particles of our invention may be either single screw or double screw. Thus, the types of extruder that can be used are disclosed at pages 246–257 and 332–349 of the Modern Plastics Encyclopedia, 1982–1983, published by the McGraw-Hill Publishing Company, the disclosure of which is incorporated by reference herein. More specifically, examples of extruders which are usable in carrying out one of the processes of our invention (with modification for introduction of the semiochemical) downstream from the introduction of the polymer and with further modification that the gaseous blowing agent is introduced still further downstream from a point of introduction of the semiochemical, e.g., a bisabolene isomer containing composition of our invention are as follows:

1. The Welex "Super Twinch", 3.5" extruder manufactured by Welex Incorporated, 850 Jolly Road, Blue Bell, Pa. 19422.
2. Krauss-Maffei twin screw extruder manufactured by the Krauss-Maffei Corporation/Extruder Division, 3629 West 30th Street South, Wichita, Kan. 67277.
3. Modified Sterling, Model 4000 and 5000 series extruder manufactured by Sterling Extruder Corporation of 901 Durham Avenue, South Plainfield, N.J.
4. CRT ("Counter-Rotating Tangential") Twin Screw Extruder manufactured by Welding Engineers, Inc. of King of Prussia, Pa. 19406.
5. The Leistritz Twin Screw Dispersion Compounder manufactured by the American Leistritz Extruder Corporation of 198 U.S. Route 206 South, Somerville, N.J. 08876.
6. The ZSK Twin Screw Co-Rotating Extruder manufactured by the Werner & Pfleiderer Corporation of 6763 East Crescent Avenue, Ramsey, N.J. 07446.
7. The Farrel Extruder manufactured by Farrel Connecticut Division, Emhart Machinery Group, Ansonia, Conn. 06401.
8. The MPC/V Baker Perkins Twin Screw Extruder manufactured by the Baker Perkins Inc. Chemical Machinery Division of Saginaw, Mich. 48601.
9. The Berstorff single screw, twin screw, or foam extrusion equipment manufactured by Berstorff Corporation, P.O. Box 240357, 8200-A Arrowridge Boulevard, Charlotte, N.C. 28224.

In producing the semiochemical, a bisabolene isomer containing composition of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate; and (e) acrylic acid including the hydrolyzed co-polymer of ethylene and vinyl acetate. Preferred co-polymers are polyethylene-vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. DuPont de Nemours Company under the tradename "ELVAX ®" and by the Arco Polymer Division under the trademark "DYLAN ®" and by the Exxon Corporation of Linden, N.J. under the trademark "DEXXON ®". Ethylene/ethyl acrylate co-polymers are market Union Carbide Corporation under the tradename "EEA RESINS ®".

The polymer is added to the single screw or twin screw extruder at a feed rate in the range of from about 80 up to about 300 pounds per hour while maintaining the temperature of the screw extruder between about 160° and about 240° C. If the polymer or co-polymer powder is added to the extruder at a reference "barrel segment", a bisabolene isomer containing composition is added to the extruder under pressure downstream from the addition point of the polymer at one or more of "barrel segments" S-2, S-3, S-4, S-5, S-6, S-7, S-8 or S-9 (referring to FIG. 7 briefly described, supra, and described in detail, infra.

The proportion of a bisabolene isomer composition containing composition of our invention to resin can vary from small but effective amounts on the order of about 1% of the weight of resin body up to about 45% by weight of the resin body. In general it is preferred to use between about 5% up to about 30% based on the weight of the resin body of a bisabolene isomer containing composition. This is an optimum amount balancing the proportion of a bisabolene isomer containing composition against the time period over which the article emits the bisabolene isomer containing composition and against the tendency of a bisabolene isomer containing composition to "oil out". This "oiling out" is specifically avoided as a result of use of the foaming agent discussed, infra.

Various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.

(b) DYLITE® of expandable polystyrene compositions. DYLITE® is a trademark of the Atlantic Richfield Company of Los Angeles, Calif.
(c) SUPER DYLAN® is a high density polyethylene, SUPER DYLAN® is a trademark of the Atlantic Richfield Company of Los Angeles, Calif.
(d) Blended polyethylene and carbon black as specifically taught in U.S. Pat. No. 4,369,267 issued on Jan. 18, 1983, the specification for which is incorporated by reference herein.
(e) Polystyrene as disclosed in U.S. Pat. No. 4,369,227 issued on Jan. 18, 1983, the specification for which is incorporated by reference herein.
(f) Polyene/alpha-olefin as exemplified and disclosed in U.S. Pat. No. 4,369,291, the specification for which is incorporated by reference herein.
(g) Poly-alpha-olefins as exemplified in Canadian Letters Patent No. 1,137,069 issued on Dec. 7, 1982, the specification for which is incorporated by reference herein.
(h) Polymeric compositions as disclosed in Canadian Letters Patent No. 1,137,068 issued on Dec. 7, 1982, the specification for which is incorporated by reference herein.
(i) Poly-alpha-olefins disclosed in Canadian Letters Patent No. 1,137,067, the specification for which is incorporated by reference herein.
(j) Polyolefins described in Canadian Letters Patent No. 1,137,066, the specification for which is incorporated by reference herein.
(k) Polyethylene oxides as disclosed in Canadian Letters Patent No. 1,137,065 issued on Dec. 7, 1982, the specification for which is incorporated by reference herein.
(l) Olefin polymers and co-polymers as disclosed in Canadian Letters Patent No. 1,139,737, the disclosure of which is incorporated by reference herein. Canadian Patent No. 1,139,737 was issued on Jan. 18, 1983.
(m) Polyolefins disclosed in Canadian Letters Patent No. 1,139,738, the disclosure of which is incorporated by reference herein. Canadian Patent No. 1,139,738 was issued on Jan. 18, 1983.
(n) Chlorinated PVC as disclosed in Polymer 1982, 23 (7, Suppl.), 1051-6 abstracted at Chem. Abstracts 97:145570y, 1982.
(o) Polyepsilon caprolactone co-polymers made by means of alcohol initiated polymerization as disclosed in J. Polym. Sci. Polym. Che. Ed., 1982, 20(2), pages 319-26, abstracted at Chem. Abstracts, Volume 96:123625x, 1982.
(p) Styrene acrylonitrile co-polymers as disclosed in Diss. Abstracts, Int. B, 1982, 42(8), 3346 and abstracted at Chem. Abstracts 96:143750n (1982).
(q) Co-polymers of epsilon caprolactone with 1,4-butane diol as disclosed at Kauch. Rezine, 1982, (2), 8-9, abstracted at Chem. Abstracts, Volume 96:182506g (1982).
(r) Polyesters as disclosed in U.S. Pat. No. 4,326,010, the specification for which is incorporated by reference herein.
(s) Chlorinated polyethylene as disclosed by Belorgey, et al, J. Polym. Sci. Polym. Phys. Ed., 1982, 20(2), 191-203.
(t) Plasticized polyepsilon caprolactone co-polymers containing dimethyl phthalate plasticizers as set forth in Japanese Patent No. J81/147844, abstracted at Chem. Abstracts, Volume 96:69984y (1982), the specification for which is incorporated by reference herein.
(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein.
(v) Polyurethane polymers having lactone backbones as disclosed in U.S. Pat. No. 4,156,067 issued on May 22, 1979, the disclosure of which is incorporated by reference herein.
(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein.
(x) Resins having polyurethane backbones as disclosed in U.S. Pat. No. 3,975,350 issued on Aug. 17, 1976, the disclosure of which is incorporated by reference herein.

Downstream from the addition point of a bisabolene isomer containing composition, optionally, the gaseous or liquid containing blowing agent may be added (e.g., at barrel segments S-5, S-6, S-7, S-8, S-9 or S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of a bisabolene isomer containing composition containing particle.

The feed rate range of a bisabolene isomer containing composition may be between about 0.5% up to about 45% by weight of the polymer.

The die of the extruder may create rod, sheet film or ribbon. The resulting product may then, if desired, be pelletized to form a bisabolene isomer containing composition or a bisabolene isomer containing composition containing polymer particles or the ribbon may be used "as is" as a bisabolene isomer containing composition containing polymeric article of manufacture itself.

In addition to the optional gaseous blowing agents (which are necessarily "inert" gases), blowing agents may be added at the same point on the extruder which will create gaseous voids in the bisabolene isomer containing composition-containing polymer articles of our invention and these "blowing agents" are well known to one having ordinary skill in the art.

Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFC_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which is incorporated by reference herein; and (iv) Azo bis (formamide); diazoaminobenzene; N,N'-di nitrosopentamethylene tetramine; N,N'-dimethyl-N-N'-dinitrosoterephthalamide; p,p'-oxy-bis-(benzene sulfonyl semicarbazide); azo bis-(isobutyronitrile); p,p'-oxy-bis (benzene sulfonyl hydrazide); p,p'-diphenyl-bis (sulfonyl hydraxide); benzene-sulfonyl hydrazide; m-benzene-bis (sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming and which contain the bisabolene isomer containing composition of our invention in order to repel at least one of the insect species:
(a) *Musca domestica* L.;( *Diptera Muscidae*); and/or
(b) *Aedes aegypti.*

The insect repellent-perfume compositions which form part of the candle body materials are within the following specification:

(I) from 5 up to 100% by weight of an efficacious perfume/insect repellent composition consisting essentially of a bisabolene isomer containing composition of our invention; and (II) from 0 up to 95% of a standard perfuming susbstance (not necessarily insect repellent) which may be one or a combination of the following materials:
the methyl ester of 2,5-dihydroxy-4,6-dimethyl benzoic acid;
dihydro myrcenol;
oakmoss absolute;
benzyl acetate;
geraniol;
isobornyl acetate;
citronellyl acetate;
para-t-butyl phenyl isovaleraldehyde;
benzyl salicylate;
hexyl cinnamic aldehyde;
geranonitrile;
patchouli oil;
alpha-terpineol;
tetrahydromuguol;
phenyl ethyl alcohol;
cedrenal;
methyl ionone;
cinnamyl acetate;
benzyl benzoate;
L-Citronellal;
nerol;
geranyl formate;
geranyl acetate;
eugenol;
alpha Farnesene;
beta Farnesene;
citral;
n-Nonanal;
n-Octanal; and
trans, trans delta-damascone.

The foregoing formulae may require a solubilizing agent, e.g., the methyl of dihydroabietic acid (commerical name: HERCOLYN D ®), benzyl benzoate, isopropyl myristate and/or $C_{12}$–$C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:
(i) a thermoplastic polyamide resin formed from linoleic acid polymerized with a polyamine compound;
(ii) an alkanol amide or alkanol amine; and
(iii) a stearic acid compound.

The weight of ratio of candle body: a bisabolene isomer containing composition perfumant substance of our invention may vary from about 0.8% up to about 10% with a range of from about 0.8% up to about 2.0% being preferred when no non-insect repelling perfume oil is used in conjunction with a bisabolene isomer containing composition of our invention; and with a range of from about 1.5% up to about 10% by weight of the overall composition being preferred when a non-insect repelling perfume oil is used in conjunction with the bisabolene isomer containing composition of our invention.

Specifically, the polyamide may be a "Versamid" resin which is a thermoplastic condensation product of polymerized linoleic acid with various polyamine compounds such as ethylene diamine, ethylene triamine and the like. Specific "Versamid" compounds are "VERSAMID ®900", "VERSAMID ®930", 940", "VERSAMID ®948", "VERSAMID ®950", and "VERSAMID ®1635". These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as Barlol 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of perfumant/insect repellent if part of the formula is replaced by the material "Nevex 100", a product which is a coumarin-indene copolymer resin of very little unsaturation, manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature chosen from the group consisting of light mineral oil and natural oils having iodine values substantially within the range of 40–135;

(b) from about 7% up to about 40% by weight of a long chain polyamide having a molecular weight substantially within the range of 6000–9000 and a softening point substantially within the range of 18° C.–48° C.; and (c) from about 7% up to about 30% of an alcohol selected from the group consisting of 8 to 12 carbon primary alcohols.

Such compositions may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

The following Tables I and II show the results of utilization of the olfactometer apparatus of FIG. 6 in testing for the attractancy or repellency of *Musca domestica* L. (Diptera Muscidae) and *Aedes aegypti*, using the bisabolene isomer containing composition of our invention.

TABLE I

| AEDES AEGYPTI | | | | | | | |
|---|---|---|---|---|---|---|---|
| Composition Tested | Insects Per Interval | | | | | | |
| Bisabolene isomer composition prepared according to Example I, bulked distillation fractions 7–14. | 0 | 40 | 26 | 15 | 79 | 0 | 6 |
| Air | 0 | 233 | 382 | 376 | 295 | 331 | 151 |

TABLE II

| MUSCA DOMESTICA L.(DIPTERA MUSCIDAE) | | | | | | | |
|---|---|---|---|---|---|---|---|
| Composition Tested | Insects Per Interval | | | | | | |
| Bisabolene isomer containing mixture produced according to Example I, bulked distillation fractions 7–14. | 0 | 1 | 8 | 0 | 6 | 0 | 0 |
| Air | 0 | 172 | 17 | 0 | 2 | 0 | 0 |

BRIEF DESCRIPTION OF THE DRAWINGS

FIG. 3 represents a cut-away side elevation view of apparatus used in forming perfumed polymers which contain imbedded therein at least one of the bisabolene isomer containing composition of our invention.

FIG. 4 is a front view of the apparatus of FIG. 3 looking in the direction of the arrows.

FIG. 9 is a perspective view of an ellipsodially-shaped detergent tablet containing a solid core which includes fused foamed polymeric particles which contain insect repellents which can be one of the bisabolene isomer containing compositions of our invention and, if desired, also containing an additional polymer, e.g., polyethylene. The polymer particles may, if desired, also contain additional aromatizing agents.

FIG. 10 is the top view of the ellipsodially-shaped detergent tablet of FIG. 9.

FIG. 11 is a cut-away front view of the ellipsodially-shaped detergent tablet of FIG. 9 in the direction of the arrows in FIG. 10.

FIG. 12 is a side view of the ellipsodially-shaped detergent tablet of FIG. 9.

FIG. 13 is a perspective view of a rectangular parallel-piped-shaped detergent tablet containing a rectangular parallel-piped-shaped core comprising a major proportion of fused foam polymeric particles which contain insect repellent, (e.g., the bisabolene isomer containing composition of our invention) and may or may not be aromatized and, if desired, an additional polymer which may or may not contain insect repellent compositions and which may or may not be aromatized.

FIG. 14 is a top view of the rectangular parallelpiped-shaped detergent tablet of FIG. 13.

FIG. 15 is a cut-away front view of the rectangular parallelpiped shaped detergent tablet of FIG. 13 looking in the direction of the arrows in FIG. 14.

FIG. 16 is a perspective view of an ellipsoidally-shaped detergent tablet containing a hollow insect repellent agent (and, if desired, an aromatizing agent) containing core which includes fused foamed polymeric particles (the insect repellent and, if desired, the aroma imparting agent is in the solid polymer and not in the void of the plastic core).

FIG. 17 is a top view of the ellipsoidally-shaped detergent tablet of FIG. 16.

FIG. 18 is a front cut-away view of the ellipsoidally-shaped detergent tablet of FIG. 16 looking in the direction of the arrows in FIG. 17, the core thereof being hollow and either containing an insect repellent material (and, if desired, an aroma imparting liquid) or in the alternative, being a hollow core wherein the insect repellent material (and, if desired, the aroma imparting material which may be one and the same bisabolene isomer containing mixtures of our invention) is in the solid fused foam polymeric particles which make up the core and wherein the void does not contain anything.

DETAILED DESCRIPTION OF THE DRAWINGS

Figure 1:
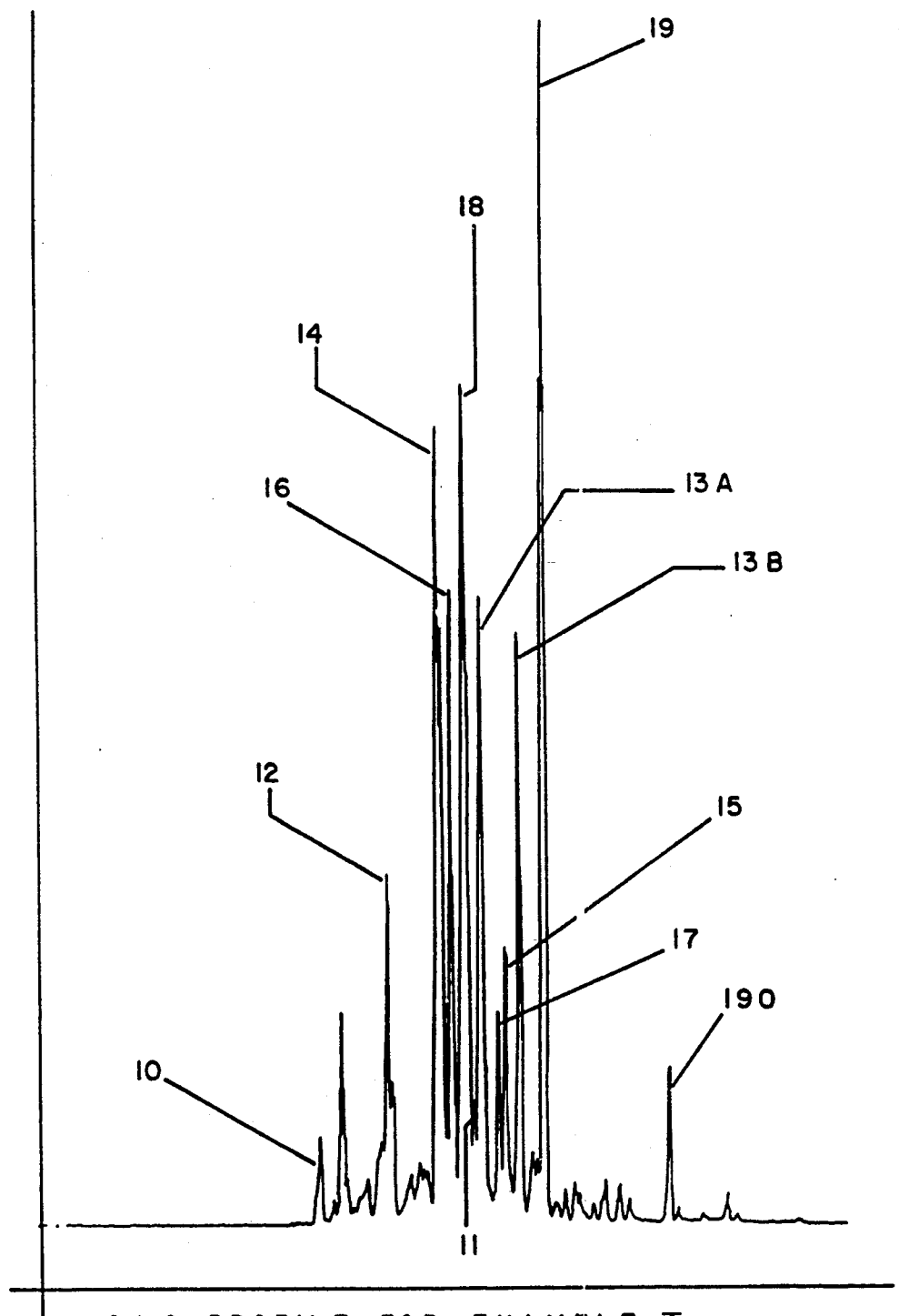
FIG. 1 is the GLC profile for the reaction product prepared according to Example I containing a ratio of bisabolene isomers:farnesene isomers of 54.8:8.7 (Conditions: OV-1 capillary survey).

Referring to FIG. 1, FIG. 1 is the GLC profile for the reaction product of Example I containing bisabolene isomers of our invention prepared by means of dehydration of cabreuva oil using a citric acid catalyst (Conditions: OV-1 capillary survey). The peak indicated by reference numeral 10 is the peak for trans-beta-farnesene defined according to the structure:

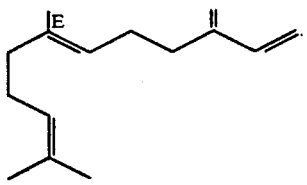

The peak indicated by reference numeral 11 is the peak for the compound having the structure:

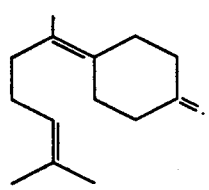

The peak indicated by reference numeral 12 is the peak for gamma curcumene having the structure:

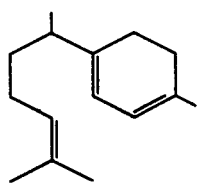

The peak indicated by reference numeral 14 is the peak for a mixture of cis-alpha-beta-bisabolene having the structure:

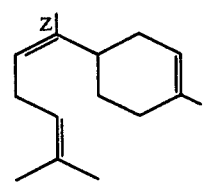

and epizonarene having the structure:

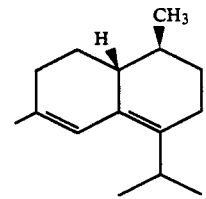

The peak indicated by reference numeral 16 is the peak for trans,trans-alpha-farnesene having the structure:

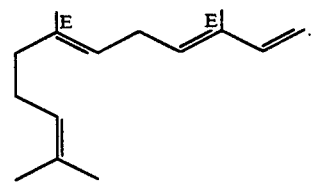

The peak indicated by reference numeral 18 is the peak for beta-bisabolene having the structure:

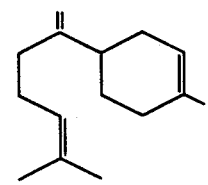

The peaks indicated by reference numerals 13A and 13B are for gamma-bisabolene having the structure:

The peak indicated by reference numeral 19 is for trans, alpha-bisabolene having the structure:

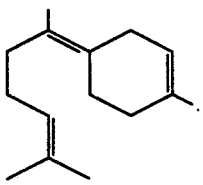

The peak indicated by reference numeral 17 is for delta-cadinene having the structure:

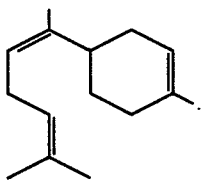

The peak indicated by reference numeral 15 is for a zonarene isomer having the structure:

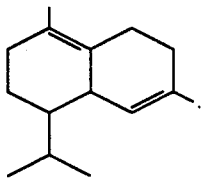

The peak indicated by reference numeral 190 is for allofarnesene having the structure:

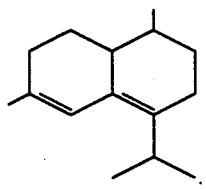

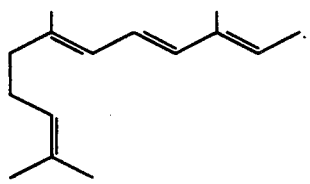

(Conditions: 50 meter×0.32 mm fused silica methyl silicone column programmed at 75°-225° C. at 2° C. per minute).

Figure 2:
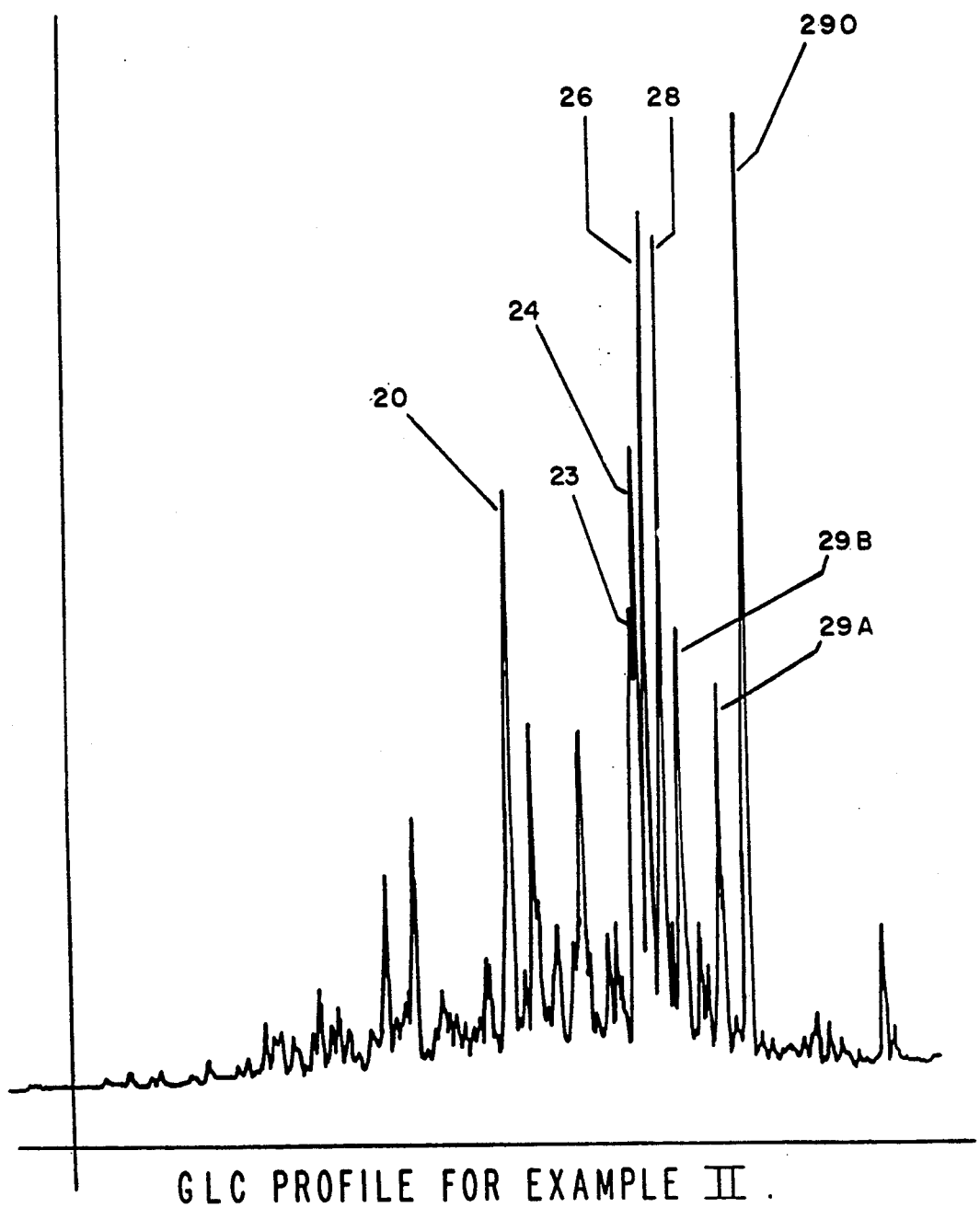
FIG. 2 is the GLC profile for the reaction product of Example II containing bisabolene isomers.

FIG. 2 is the GLC profile for the reaction product of Example II for a bisabolene isomer containing mixture prepared from cabreuva oil using a phosphoric acid catalyst. (Conditions: 50 meter×0.32 mm fused silica methyl silicone column programmed at 75°-225° C. at 2° C. per minute). The peak indicated by reference numeral 20 is the peak for trans-beta-farnesene having the structure:

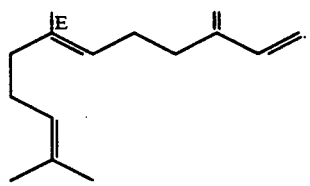

The peak indicated by reference numeral 22 is the peak for epizonarene having the structure:

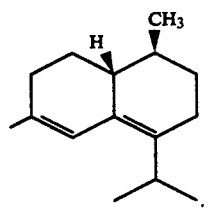

The peak indicated by reference numeral 24 is the peak for cis-alpha-bisabolene having the structure:

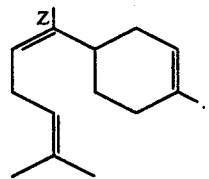

The peak indicated by reference numeral 26 is the peak for trans,trans,alpha farnesene having the structure:

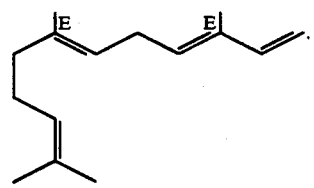

The peak indicated by reference numeral 28 is the peak for beta-bisabolene having the structure:

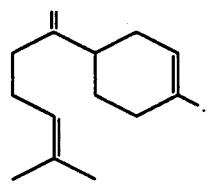

The peaks indicated by reference numerals 29A and 29B are for gamma-bisabolene having the structure:

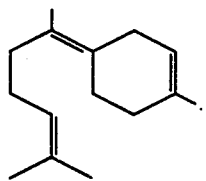

The peak indicated by reference number 290 is the peak for trans,alpha-bisabolene having the structure:

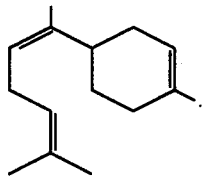

Referring to FIGS. 3 and 4, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 3 and 4, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least a mixture of the bisabolene isomers of our invention and other compatible perfumes (if desired) is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to container 212 is heated from 10–12 hours, whereafter the perfume composition or perfume material which contains a bisabolene isomer containing composition of our invention is quickly added to the melt. Generally, about 10–45 percent by weight of the resulting mixture of the perfumery substance is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the bisabolene isomer containing mixture of our invention or mixture of bisabolene isomer containing mixture of our invention and one or more other substances, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains a large portion of the bisabolene isomer containing composition of our invention, through the orifices 234 at a rate which will insure the formation of droplets 236 which will fall downwardly onto a moving conveyor 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageoulsy filled with water or some other suitable cooling liquid to insure the rapid cooling of each of the pellets 244. The pellets 244 are then collected from the container 250 and utilized for the formation of other functional products, e.g., garbage bags which are not only pleasantly smelling and which cover unpleasant garbage odor but which are also insect repellent.

Figure 5:
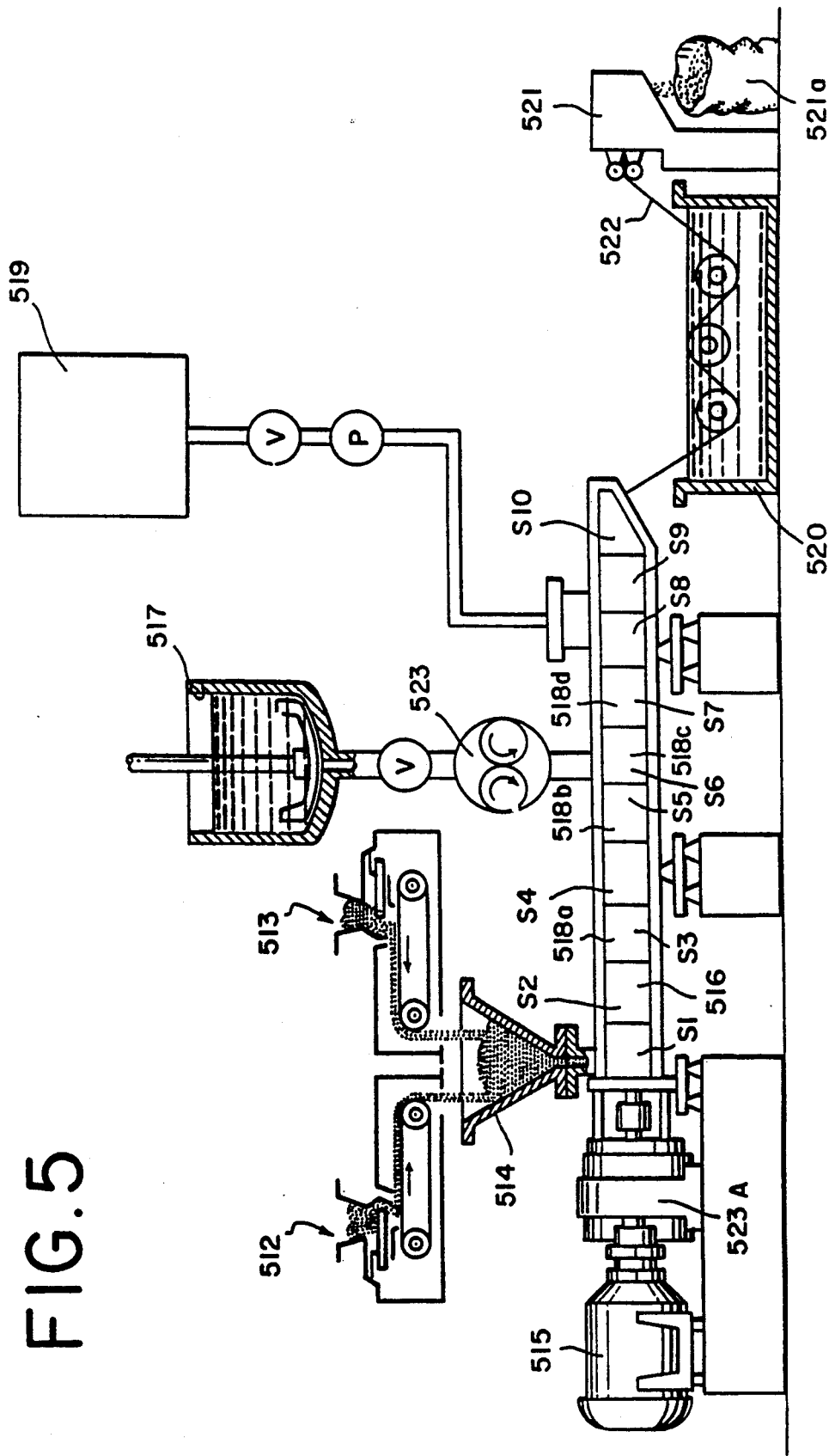
FIG. 5 is a cut-away side elevation schematic diagram of a screw extruder operating during compounding of a polymer (e.g., polyethylene) with a bisabolene isomer containing composition of our invention while simultaneously adding foaming agent into the hollow portion of the barrel of the extruder and incorporates the pelletizing apparatus used in pelletizing extruded foamed tow produced as a result of the extrusion operation.

FIG. 5 is a schematic cut-away elevation diagram of the extrusion and pelletizing apparatus useful in carrying out a process used in reducing our invention to practice. During the operation of said apparatus, motor 515 drives the extruder screws located at 523A in barrel 516, the extruder being operated at temperatures in the range of about 150° up to about 250° C. At the beginning of the barrel, resin at source 512 together with processing aids at location 513 is added via addition funnel 514 into the extruder. Simultaneously (when the operation reaches "steady state"), a bisabolene isomer containing composition of our invention is added to the extruder at two or more of barrels S-3, S-4, S-5, S-6, S-7 and S-8 of the extruder (which may be a twin screw or single screw extruder) at locations 518a, 518b, 518c and 518d, for example, by means of gear pump 523 from source 517. From source 519 into barrel segments S-5, S-6, S-7, S-8, S-9 and S-10, optionally, the gaseous or liquid blowing agents, e.g., nitrogen, carbon dioxide and the like as described, supra, are added simultaneously with the addition of a bisabolene isomer containing composition of our invention. The feed rate range of resin is about 80–300 pounds per hour. The feed rate range of a bisabolene isomer containing composition of our invention is between 1 and 35% of the feed rate range of the resin. The blowing agent rate range (when the blowing agent is used) is such that the pressure of the gas or the pressure over the liquid being fed into the extruder is between about 50 and 200 psig. If desired, the extruder ribbon or cylinder may be passed through water bath 520 and pelletizer 521 into collection apparatus 521a.

Figure 6:
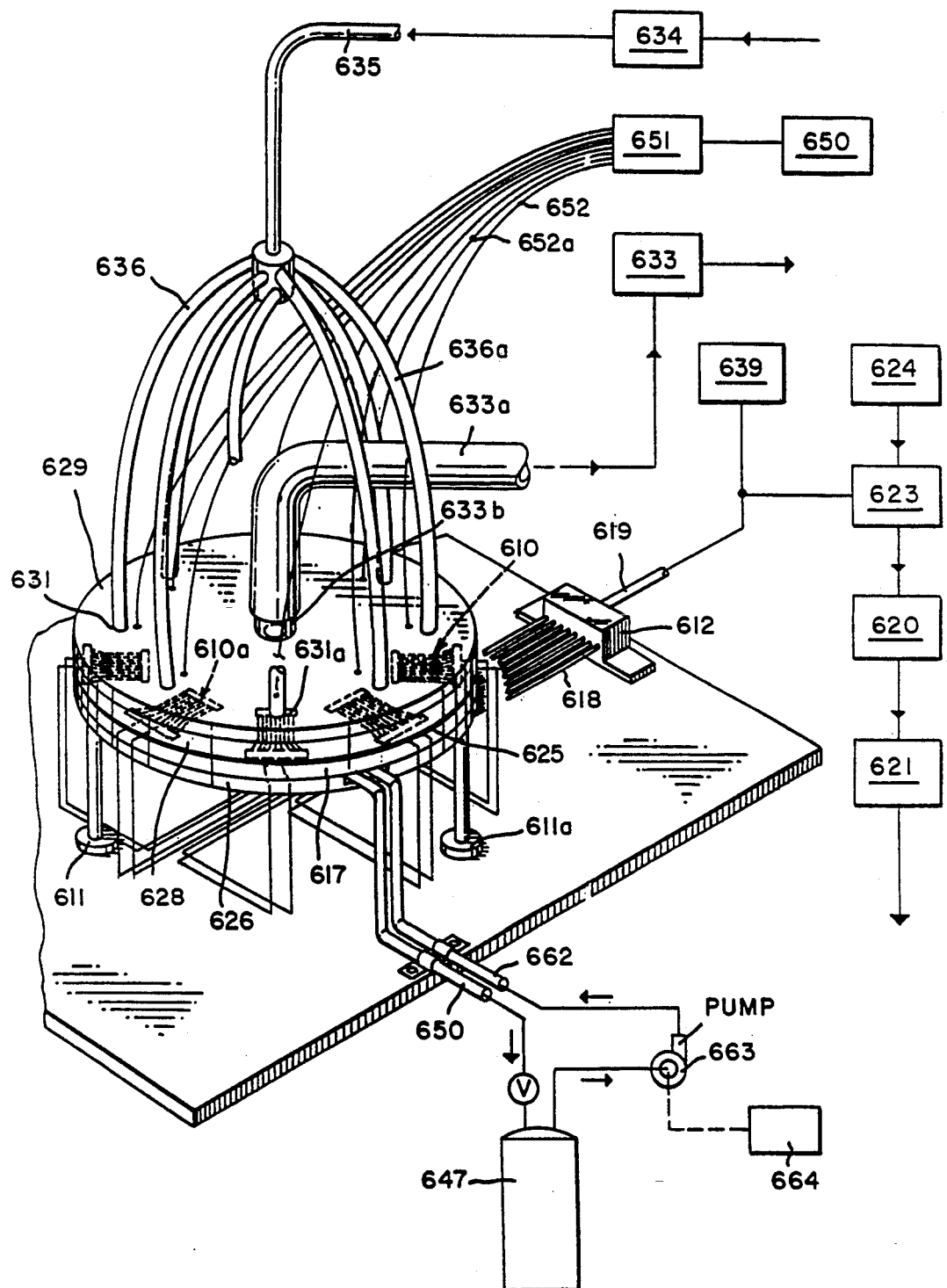
FIG. 6 is a schematic diagram of olfactometer apparatus of the prior art, U.S. Pat. No. 4,764,367 issued on Aug. 16, 1988 (incorporated by reference herein) useful in ascertaining the efficacy of the bisabolene isomer-containing compositions of our invention as repellents against house flies (*Musca domestica* L.(Diptera Muscidae)) as well as mosquitoes (*Aedes aegypti*) and also indicates in schematic block flow diagram form the utilization of computer-assisted efficacy measuring apparatus.

FIG. 6 is a perspective schematic diagram of olfactometer apparatus of the prior art (U.S. Pat. No. 4,764,367 issued on Aug. 16, 1988, the specification for which is incorporated by reference herein) used in testing the efficacy of the bisabolene isomer containing compositions of our invention as house flies (*Musca domestica* L.(Diptera Muscidae)) repelling materials and as mosquito (Aedes aegypti) repelling materials. Air source 634 feeds air through line 635 through air distributor 636, 636a, et seq. onto base plate 617 containing insect landing site 610, 610a, et seq. The base plate 617 is separated from the spacer plate 629 for the air lines 636 whereby the air lines 636 are held in place at positions 631, 631a, et seq. Air exits through line 633a using exhaust fan 633. Simultaneously, with the air being fed through line 636, 636a, et seq., from air source 634, light is guided through light guides 652 and 652a using light source 651 powered by electric power source 650. The base plate 617 is separated from the spacer plate 629 also for the light guide 652, 652a, et seq., whereby the light guide 652, 652a, et seq., are held in place at positions 631, 631a, et seq.

The olfactometer is assisted with computer apparatus shown in schematic form and block flow diagram form using reference numeral 620, 621, 623, 624 and 639. Dampers 611a, 611b, et seq., hold base plate 617 in place horizontally.

When an insect is de-anesthetized and in action, e.g., a house fly (*Musca domestica* L.(Diptera Muscidae)) lands on a sensor landing site, the landing is recorded electrically through the sensor 610, 610a, et seq.. The sensor 610, 610a, et seq., causes an electrical impulse to proceed through wire 618 and then through wire 619 using electrical power source 639 to a multi-channel A-D converter 623 which is associated with program tape storage 624, printer 620 and digital computer associated with modem and main frame 621.

Figure 7:
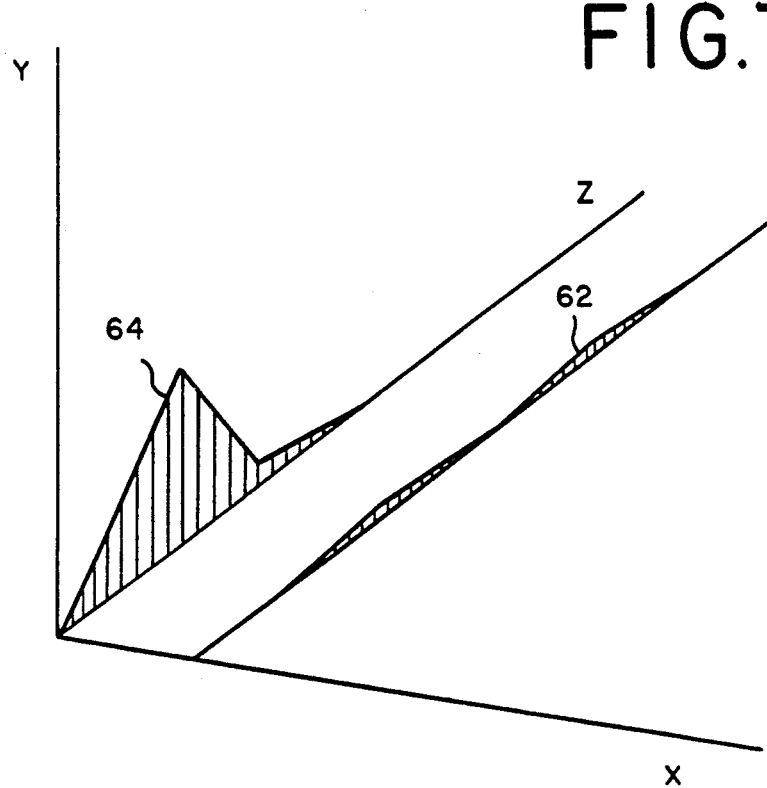
FIG. 7 is a series of graphs depicting in three dimensions (in rectangular mode for the "X" and "Y" axes) showing the relative repellency of the bisabolene isomer containing compositions of our invention versus the attractiveness of air. The graphs are based on experiments run for a total of one hour with six intervals of ten minutes each. The results are tabulated in Tables I and III, infra. The series of graphs are for the repellency against house flies (*Musca domestica* L (Diptera Muscidae)).
Figure 8:
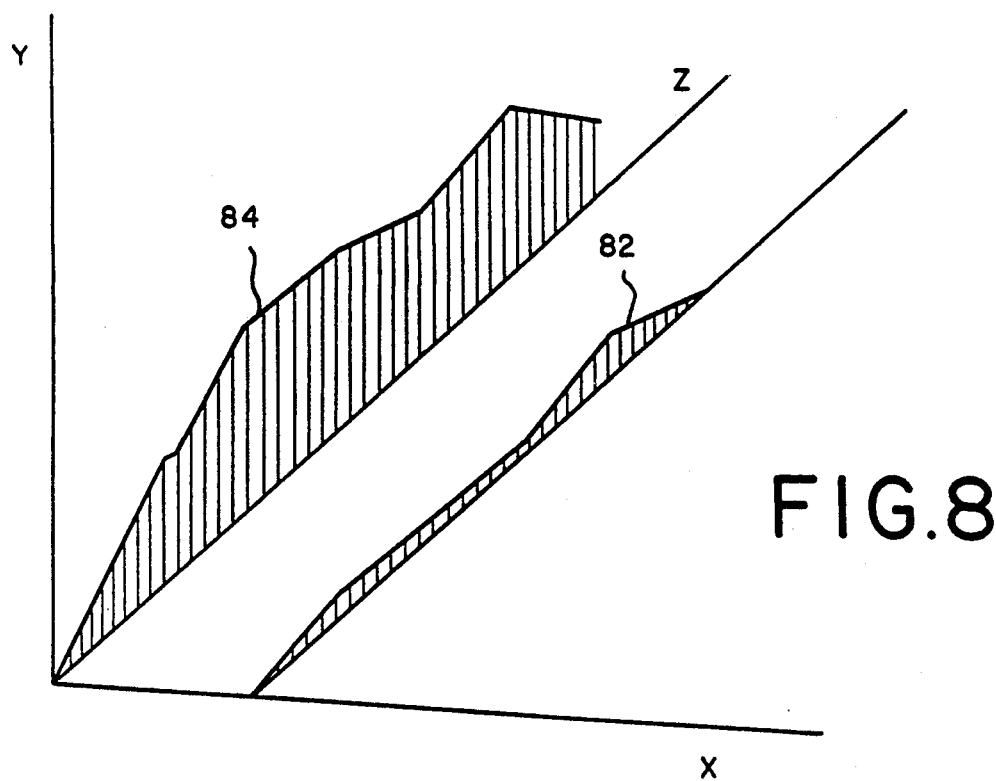
FIG. 8 is a series of graphs depicted in three dimensions (in a rectangular mode for the "X" and "Y" axes) showing the relative repellency of bisabolene isomer containing compositions of our invention versus the attractiveness of air for or against mosquitoes (*Aedes aegypti*). The graphs are based on experiments run for a period of one hour with six intervals of ten minutes each. The results are tabulated in Tables II (supra) and IV (infra).

Referring to FIGS. 7 and 8 are a series of graphs depicting in three dimensions (in a rectangular mode for the "X" and "Y" axes) showing the relative repellency of bisabolene isomer containing compositions as well as air per se. The graphs are based on experiments run for a period of one hour with six intervals of 10 minutes each.

Thus, referring to FIG. 7, FIG. 7 shows relative repellency against house flies (*Musca domestica* L.(Diptera Muscidae)) of bisabolene isomer containing compositions of Example I (the graph indicated by reference numeral 62) as compared to the attractiveness of air itself (the graph for which is indicated by reference numeral 64).

The data supporting the graph of FIG. 7 is set forth in Table II, supra, and in the following Table IV.

TABLE IV

| *MUSCA DOMESTICA* L.(DIPTERA MUSCIDAE) | | | | | | | |
|---|---|---|---|---|---|---|---|
| Composition Tested | Reference Numeral For Graph | INSECTS PER INTERVAL | | | | | |
| Bisabolene Isomer Containing Composition of Example I, (bulked, distillation) fractions 7–14. | 62 | 0 | 1 | 8 | 0 | 6 | 0 | 0 |
| Air | 64 | 0 | 172 | 17 | 0 | 2 | 0 | 0 |

Referring to FIG. 8, FIG. 8 shows the relative repellency of bisabolene isomer containing compositions with reference to clean air (as an "attractant" against the species of mosquito (Aedes aegypti). Thus, the repellency against *Aedes aegypti* of bisabolene isomer containing compositions is shown in the graph indicated by reference numeral 82. The attractancy for *Aedes aegypti* of clean air (relative humidity 75–80%) is shown by the graph indicated by reference numeral 84. The data supporting the graphs set forth in FIG. 8 are set forth in the following Table III.

TABLE III

| *AEDES AEGYPTI* | | | | | | | |
|---|---|---|---|---|---|---|---|
| Composition Tested | Reference Numeral For Graph | INSECTS PER INTERVAL | | | | | |
| Bisabolene Isomer Containing Composition of Example I, (bulked, distillation) fractions 7–14. | 82 | 0 | 40 | 26 | 15 | 79 | 0 | 6 |
| Air | 84 | 0 | 233 | 382 | 376 | 295 | 331 | 151 |

DETAILED DESCRIPTION OF THE DRAWINGS

A preferred embodiment of our invention set forth in FIGS. 9–18 comprises an ellipsoidally-shaped detergent tablet 830 containing a solid plastic core 832 which can be fabricated from, for example, polyethylene, polypropylene, nylon or any polymer capable of having therein microvoids from which an insect repelling substance, e.g., bisabolene isomer containing compositions of Example I or II will be controllably transported from the plastic core into and through the soap cake over a reasonable period of time during the use of the soap cake. Such polymers can be microporous polymers such as those described in U.S. Pat. No. 4,247,498 issued on Jan. 27, 1981, the specification for which is incorporated herein by reference. Surrounding the central plastic core containing insect repellent 832 is detergent 830' which is in the solid phase at ambient conditions, e.g., room temperature and atmospheric pressure. Examples of workable detergents 830' are "elastic" detergents such as those described in U.S. Pat. No. 4,181,632 issued on Jan. 1, 1980, the disclosure of which is incorporated herein by reference, or "transparent" soaps such as those set forth in U.S. Pat. No. 4,165,293 issued on Aug.

21, 1979, the disclosure of which is incorporated herein by reference. Other examples of the detergent 830' useful in our invention are those set forth as "variegated soaps" in Canadian Letters Patent No. 1,101,165 issued on May 19, 1981, the disclosure of which is incorporated by reference herein.

On use of the soap tablet 830 or detergent bar, the insect repellent agent, e.g., the bisabolene isomer containing composition of Example I or II, originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelpiped tablet as shown in FIGS. 13, 14 and 15 containing solid plastic core 839. The insect repellent located in solid plastic core 839 on use of the detergent bar passes through at steady state, surface 832 of FIG. 14, detergent 838 and finally surface 839 at, for example, locations 840, 841, 842 and 843. The environment surrounding the detergent bar on use thereof is then treated with insect repellent, e.g., the bisabolene isomer containing composition of Example I or II, at 843, 844 and 845. Optionally, aromatizing agent can also be contained (in addition to the bisabolene isomer containing composition of our invention) in the detergent bar and so the environment surrounding the detergent bar on use thereof would also be aesthetically aromatized at 843, 844 and 845, for example, with aromatizing agents in addition to the bisabolene isomer containing composition of our invention. It must be understood that the bisabolene isomer containing composition of our invention is an aromatizing agent as well as an insect repellent agent in and of itself so additional aromatizing agent is not really necessary.

As shown in FIGS. 16, 17 and 18, the plastic core of the detergent tablet 830 may have a single finite void at its center 851 (of FIGS. 17 and 18) in which the insect repellent agent and optionally, the aromatizing agent is contained. The plastic core is then a shell 848 having outer surface 852 (shown in FIGS. 17 and 18). The insect repellent agent (and optionally, any additional aromatizing agent) contained in the void in the plastic core permeates through shell 848, past surface 852 at a steady state, through the detergent 847 and to the environment at, for example, 856, 857, 858 and 859.

In addition to the insect repellent contained in the core, e.g., core 839 or core void, the core can also contain other materials for therapeutic use, for example, bacteriostats, deodorizing agents and the like which are compatible with insect repllents such as the bisabolene isomer containing composition of our invention. In the alternative, the plastic core of the detergent tablet of FIGS. 16, 17 and 18 may have an empty single finite void at its center 851 with the insect repellent contained in the shell 848.

At the end of the use of the detergent tablet, the hollow core or the solid core can be used as an insect repelling and aroma imparting or air freshener household article. In addition, depending on the ratio of the volume of the void 851, to the solid part of the detergent tablet of FIGS. 16, 17 and 18, the detergent tablet of FIGS. 16, 17 and 18 can be so fabricated that it will float on the surface of the liquid in which it is being used and this physical attribute has certain obvious advantages.

The following Examples I and II illustrate methods of our invention used to manufacture the bisabolene isomer containing compositions of our invention. Examples following Example II serve to illustrate organoleptic utilities of the bisabolene isomer containing compositions of our invention as well as insect repellent utilities of the bisabolene isomer containing compositions of our invention.

All parts and percentages given herein are by weight unless otherwise specified.

EXAMPLE I

Preparation of Bisabolene Isomer Containing Composition

Reaction

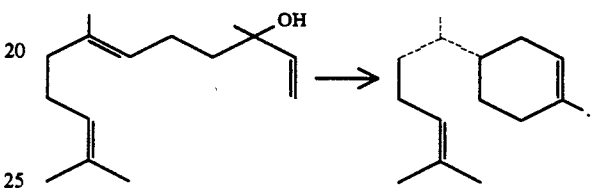

wherein in the composition defined according to the structure:

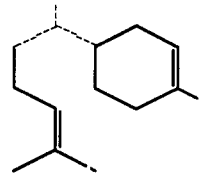

which is a mixture in the mixture in each of the compounds one of the dashed lines is a carbon-carbon double bond and each of the other of the dashed lines represent carbon-carbon single bonds.

Into a 5 liter reaction flask equipped with stirrer, thermometer, reflux condenser and water take-off apparatus (Bidwell trap) is placed 2000 ml PRIMOL® (mineral oil manufactured by the Exxon Company of Linden, N.J.); and 100 grams of citric acid. With stirring the resulting mixture is heated to a temperature in the range of 160°–165° C. Over a period of one hour while maintaining the reaction temperature at 160°–166° C., one kilo of Cabreuva oil containing 86.5% nerolidol having the structure:

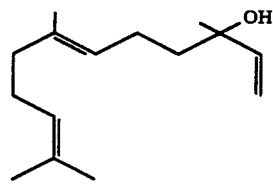

is added to the reaction mass while removing water simultaneously to the addition of the nerolidol. At the end of the one hour addition period, additional water is removed.

While maintaining the reaction mass at 166° C., the reaction mass is refluxed while removing additional water of reaction. The refluxing takes place for an additional one hour.

The reaction mass is then cooled to 40° C. and transferred to a 12 liter separatory funnel containing 2 liters of n-hexane. The phases are separated. The organic phase is washed with 200 ml 5% sodium hydroxide. The organic phase is then washed with an additional 500 ml saturated sodium chloride. The organic phase is then distilled on a rushover column at 120°-131° C. at 5.8-6.6 mm/Hg. The resulting product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 85/103 | 140/140 | 2.3/3.01 |
| 2 | 95 | 136 | 2.9 |
| 3 | 92 | 136 | 2.9 |
| 4 | 102 | 138 | 2.8 |
| 5 | 102 | 138 | 2.8 |
| 6 | 108 | 144 | 2.9 |
| 7 | 108 | 144 | 2.8 |
| 8 | 108 | 144 | 2.8 |
| 9 | 110 | 140 | 3.2 |
| 10 | 112 | 142 | 2.9 |
| 11 | 114 | 144 | 3.0 |
| 12 | 114 | 142 | 2.8 |
| 13 | 120 | 148 | 2.9 |
| 14 | 124 | 205 | 2.9. |

The resulting product contains a majority of isomers of bisabolene having the structures:

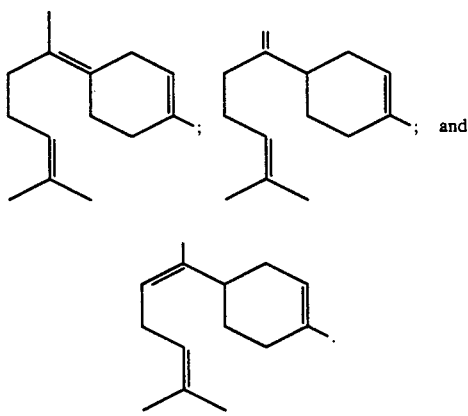

In addition, the resulting product also contains compounds having the structures:

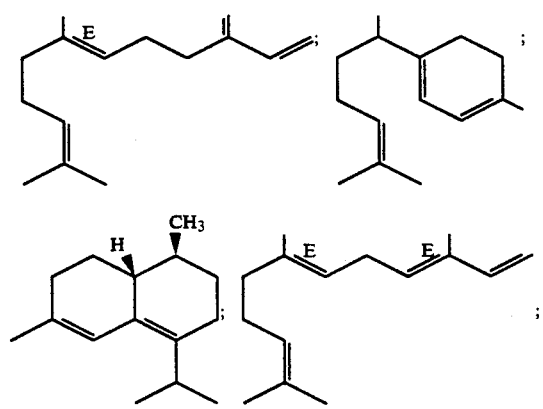

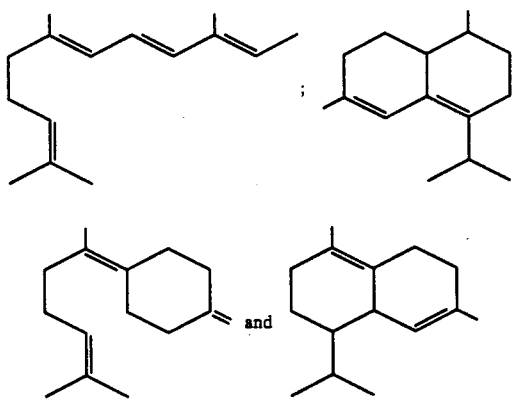

and the composition is shown in the GLC profile of FIG. 1 as described in detail, supra.

The resulting product has an intense, natural, dry, floral, opoponax aroma, with floral, freesia, fruity, citrus, bergamot, mango and opoponax topnotes (bulked distillation fractions 7-14).

EXAMPLE II

Preparation of Bisabolene Isomer Containing Composition

Reaction

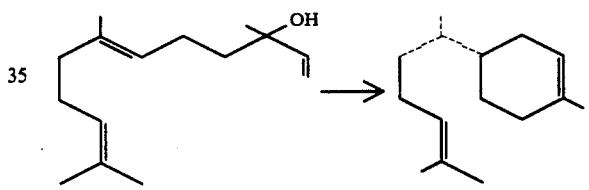

wherein in the product defined according to the structure:

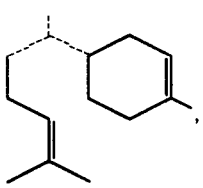

a mixture, in the mixture in each of the compounds one of the dashed lines is carbon-carbon double bond and each of the other of the dashed lines is a carbon-carbon single bond.

Into a 500 ml reaction flask equipped with stirrer, thermometer, condenser and Dean Stark water removal trap is placed 15 grams of phosphoric acid and 150 ml PRIMOL ®. The reaction mass is heated to 160°-165° C. with stirring. Over a nerolidol is added to the reaction mass, while maintaining the reaction mass at 158°-164° C.

The reaction mass is then cooled to room temperature.

The reaction mass is then placed in a separatory funnel and is washed with two 100 ml volumes of water followed by 100 ml of 1% sodium hydroxide.

The organic phase is then distilled at a vapor temperature of 135° C. and vacuum of 2.5 mm/Hg. yielding a product containing a majority of bisabolene isomers having the structures:

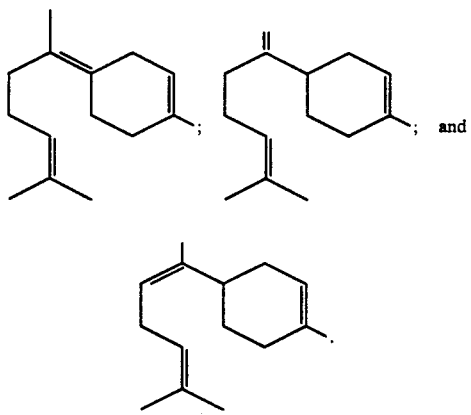

The reaction product GLC profile is set forth in FIG. 2 and described in detail, supra.

The resulting reaction product has an intense, natural, dry, floral, opoponax aroma, with floral, freesia, fruity, citrus, bergamot, mango and opoponax topnotes.

EXAMPLE III

Preparation of Ginger Fragrance Formulation

The following ginger fragrance formulations are prepared:

| INGREDIENTS | PARTS BY WEIGHT EXAMPLE (IIIA) | EXAMPLE (IIIB) |
|---|---|---|
| Ginger Essential Oil | 12 | 12 |
| Lime Distilled Essential Oil | 8 | 8 |
| Orange Essential Oil | 8 | 8 |
| Vanillin | 4 | 4 |
| Cinnamaldehyde | 6 | 6 |
| Isoeugenol | 4 | 4 |
| Eugenol | 2 | 2 |
| Terpineol | 6 | 6 |
| Hexyl Cinnamic Aldehyde | 3.2 | 3.2 |
| Bisabolene Isomer Containing Composition of Example I, bulked distillation, fractions 7-14 | 6 | 0 |
| Bisabolene Isomer Containing Composition of Example II | 0 | 6 |

The ginger fragrance formulation of Example (IIIA) can be described as "ginger, having natural, dry, floral and opoponax undertones, with floral, freesia, fruity, citrus, bergamot, mango and opoponax topnotes".

The ginger formulation of Example (IIIB) can be described as "ginger, having natural, dry, floral, and opoponax undertones, with floral, freesia, fruity, citrus, bergamot, mango and opoponax topnotes".

EXAMPLE IV

Preparation of Cosmetic Powder Compositions

Cosmetic powder compositions are prepared by mixing in a ball mill 100 grams of talcum powder with 0.25 grams of each of the substances set forth in Table V below. Each of the cosmetic powder compositions has an excellent aroma as described in Table V below:

TABLE V

| Substance | Aroma Description |
|---|---|
| Bisabolene isomer-containing composition produced according to Example I, bulked distillation, fractions 7-14. | A natural, dry, floral, opoponax aroma, with floral, freesia, fruity, citrus, bergamot, mango and opoponax topnotes. |
| Bisabolene isome-containing composition of Example II. | A natural, dry, floral, opoponax aroma, with floral, freesia, fruity, citrus, bergamot, mango and opoponax topnotes. |
| Perfume composition of Example III(A). | Ginger, having natural, dry, floral and opoponax undertones, with floral, freesia, fruity, citrus, bergamot, mango and opoponax topnotes. |
| Perfume composition of Example III(B). | Ginger, having natural, dry, floral, and opoponax undertones, with floral, freesia, fruity, citrus, bergamot, mango and opoponax topnotes. |

EXAMPLE V

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table V of Example IV are prepared containing 0.10%, 0.15%, 0.20%, 0.25%, 0.30% and 0.35% of the substance set forth in Table V of Example IV. They are prepared by adding and homogeneously mixing the appropriate quantity of substance set forth in Table V of Example IV below in the liquid detergent. The detergents all possess excellent aromas as set forth in Table V of Example IV, the intensity increasing with greater concentrations of substance as set forth in Table V of Example IV.

EXAMPLE VI

Preparation of Colognes and Handkerchief Perfumes

Compositions as set forth in Table V of Example IV are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table V of Example IV are imparted to the colognes and to the handkerchief perfumes at all levels indicated.

EXAMPLE VII

Preparation of Soap Compositions

One hundred grams of soap chips [per sample] (IVORY ®, produced by the Procter & Gamble Company of Cincinnati, Ohio), are each mixed with one gram samples of substances as set forth in Table V of Example IV until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table V of Example IV.

EXAMPLE VIII

Preparation of Solid Detergent Compositions

Detergents are prepared using the following ingredients according to Example I of Canadian Patent No. 1,007,948:

| Ingredient | Percent by weight |
| --- | --- |
| "NEODOL ® 45-11 (a $C_{14}$-$C_{15}$) alcohol ethoxylated with 11 moles of ethylene oxide | 12 |
| Sodium carbonate | 55 |
| Sodium citrate | 20 |
| Sodium sulfate water brighteners | q.s. |

This detergent is a phosphate-free detergent. Samples of 100 grams each of this detergent are admixed with 0.10, 0.15, 0.20 and 0.25 grams of each of the substances as set forth in Table V of Example IV. Each of the detergent samples has an excellent aroma as indicated in Table V of Example IV.

EXAMPLE IX

Utilizing the procedure of Example I at column 15 of U.S. Pat. No. 3,632,396, non-woven cloth substrates useful as dryer-added fabric softening articles of manufacture are prepared wherein the substrate, the substrate coating and the outer coating and the perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{2-22}$ HAPS
   22%—isopropyl alcohol
   20%—anti-static agent
   1%—of one of the substances as set forth in Table V of Example IV.

Fabric softening compositions prepared according to Example I at column 15 of U.S. Pat. No. 3,632,396 having aroma characteristics as set forth in Table V of Example IV, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table V of Example IV is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table V of Example IV.

EXAMPLE X

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table V of Example IV. | 0.10 |

The perfuming substances as set forth in Table V of Example IV add aroma characteristics as set forth in Table V of Example IV which are rather intense and aesthetically pleasing to the users of the soft-feel, good-hold pump hair sprays.

EXAMPLE XI

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C).

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table V of Example IV is added to the mixture. The resulting mixture is cooled to 40° C. and blending is carried out for an additional one hour in each case. At the end of this blending period, the resulting material has a pleasant fragrance as indicated in Table V of Example IV.

EXAMPLE XII

Tobacco Formulations

Tobacco mixtures are prepared by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrates | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above stated tobacco flavor formulation is applied at the rate of 1.0% to all of the cigarettes produced using the above tobacco formulation. The cigarettes are divided into groups as follows:

Group A—treated with 500 ppm of the bisabolene isomer containing mixture produced according to Example I, bulked distillation Fractions 7–14.

Group B—treated with 500 ppm of the bisabolene isomer containing composition of Example II.

Group C—not treated with any compounds (control cigarettes).

The control cigarettes and the experimental cigarettes of Groups A and B, which contain bisabolene isomer containing compositions produced according to Examples I and II, are evaluated by paired comparison and the results are as follows:

The experimental cigarettes of Groups A and B are found to have more body in tobacco smoke flavor and a fuller body sensation. The tobacco notes are described as "Turkish-like" with oriental nuances both prior to and on smoking in the main stream and the side stream. The flavor of the tobacco on smoking is, in addition, sweeter and more aromatic. All of the cigarettes are evaluated for smoke flavor with a 20 mm cellulose acetate flavor.

EXAMPLE XIII

Blackberry Jam

At the rate of 0.15 ppm, a composition of bisabolene-containing isomers produced according to Example-I, bulked distillation Fractions 7–14 is added to SMUCKER ® Blackberry Preserves. The resulting blackberry preserves retain their original fresh flavor but also have interesting ginger nuances after being removed from the vacuum jar in which it was originally marketed and the original blackberry flavor with natural-like nuances is retained for a period of six weeks when the resulting preserves are refrigerated in a standard kitchen refrigerator.

EXAMPLE XIV

Paraffin Wax Candle Body

| Ingredients | Parts by Weight |
| --- | --- |
| Paraffin wax | 95.0 |
| Bisabolene isomer-containing composition produced according to Example I, bulked distillation Fractions 7–14. | 5.0 |

The paraffin wax is intimately admixed at 150° C. and 10 atmospheres pressure with the bisabolene isomer composition of Example I in an autoclave with intensive shaking. The autoclave pressure is maintained with a nitrogen atmosphere. At the end of the period of one hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in Highlands, N.J., next to a very swampy area.

EXAMPLE XIII

Blackberry Jam

At the rate of 0.15 ppm, a composition of bisabolene-containing isomers produced according to Example I, bulked distillation Fractions 7–14 is added to SMUCKER ® Blackberry Preserves. The resulting blackberry preserves retain their original fresh flavor but also have interesting ginger nuances after being removed from the vacuum jar in which it was originally marketed and the original blackberry flavor with natural-like nuances is retained for a period of six weeks when the resulting preserves are refrigerated in a standard kitchen refrigerator.

EXAMPLE XIV

Paraffin Wax Candle Body

| Ingredients | Parts by Weight |
| --- | --- |
| Paraffin wax | 95.0 |
| Bisabolene isomer-containing composition produced according to Example I, bulked distillation Fractions 7–14. | 5.0 |

The paraffin wax is intimately admixed at 150° C. and 10 atmospheres pressure with the bisabolene isomer composition of Example I in an autoclave with intensive shaking. The autoclave pressure is maintained with a nitrogen atmosphere. At the end of the period of one hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly repellency. The candles are effective in preventing house flies from entering a room in which one candle is burning for a period of 10 minutes, the said room having dimensions of 6'×15'×15' having a 3'×3' open portal adjacent to a house fly-infested region in the month of August in Highlands, N.J., next to a very swampy area.

EXAMPLE XV

A transparent candle base is produced by intimately admixing the following ingredients:

| Ingredients | Parts by Weight |
| --- | --- |
| VERSAMID ® 1635 | 34.0 |
| Barlol 12C2 | 51.0 |
| Butyl Stearate | 3.5 |
| NEVEX ® 100 | 5.0 |
| SPAN ® 60 | 1.5 |
| Isopropyl Isostearate | 4.0 |
| Isopropyl Myristate | 4.0 |

The foregoing mixture is placed in an autoclave and intimately admixed with a perfume-scent repellent composition which is a bisabolene isomer composition produced according to Example II.

The autoclave is sealed and heated to 180° C. under 15 atomspheres pressure and maintained with vigorous shaking for a period of five hours. At the end of the five hour period, the autoclave is depressurized (being under a nitrogen pressure atmosphere) and the autoclave is opened and the contents are then poured into cyclindrical candle molds 4" in height and 2" in diameter containing 0.125" wicks. The resulting candles have efficacious insect repellencies and have aesthetically pleasing aromas on use.

The candles are effective in preventing the following insects:
(a) *Musca domestica* L.(Diptera Muscidae); and/or
(b) *Aedes aegypti*
from entering a room in which two candles have been burning for 15 minutes, the said room having dimentions of 6'×15'×15' and having a 3'×3' open portal adjacent a house fly and mosquito infested region in Highlands, N.J., in the month of August in the temperate zone.

EXAMPLE XVI

A study was conducted to evaluate the efficacy of candles which are designated "A", "B" and "C" in repelling house flies (*Musca domestica* L.(Diptera Muscidae)).

Candle "A" contained 95% Paraffin Wax and 5% of the following composition:
100 parts by weight of a bisabolene isomer containing composition produced according to Example I, bulked distillation, Fractions 7–14; and
700 parts by weight of a perfume composition containing the following ingredients:

| Ingredients | Parts by Weight |
|---|---|
| Perfume mixture of essential oils and chemicals, to wit: the methyl ester of 2,5-dihydroxy-4,6-dimethyl benzoic acid; dihydro myrcenol; oakmoss absolute; benzyl acetate; geraniol; isobornyl acetate; citronellyl acetate; para-t-butyl phenyl isovaleraldehyde; benzyl salicylate; hexyl cinnamaic aldehyde; geranonitrile; patchouli oil alpha-terpineol; tetrahydromuguol; phenyl ethyl alcohol; cedrenal; methyl ionone; cinnamyl acetate; and benzyl benzoate | 83.8 |
| Solvent: the methyl ester of dihydroabietic acid | 4.00 |

Candle "B" contained 90% Paraffin Wax and 10% citronella oil.

Candle "C" contained only Paraffin Wax.

The candles are allowed to burn for 20 minutes and the number of house flies repelled from a house fly-infested room is recorded for the next 60 minutes with the following equipment and procedure.

MATERIALS

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult house flies (*Musca domestica*) are test insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber.

For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5 minute intervals thereafter. The number of house flies repelled were those escaping to the outside cage. For the control counts were made in a similar manner, but no candle was burned.

The same three candles were used for all four replicates. Between replicates the chamber was exhausted, the Kraft paper flooring for the chamber was replaced, and the two screened repellency cages were submerged in hot detergent water, rinsed and dried.

Results

The average percent of house flies repelled for each five minute exposure period through 60 minutes is reported in the following Table VI:

TABLE VI

House Flies Repelled At Five Minute Time Intervals
20 Minutes Post Exposure

| Sample | Replicate | Number of House Flies | Cumulative Number of House Flies Repelled at Indicated Minutes | | | | | | | | | | | Overall Percent |
|---|---|---|---|---|---|---|---|---|---|---|---|---|---|---|
| | | | 10 | 15 | 20 | 25 | 30 | 35 | 40 | 45 | 50 | 55 | 60 | |
| Untreated | 1 | 93 | 1 | 1 | 1 | 1 | 1 | 2 | 2 | 3 | 3 | 4 | 6 | 6.45 |
| (no candle | 2 | 67 | 0 | 1 | 2 | 3 | 5 | 6 | 6 | 6 | 6 | 7 | 7 | 10.45 |
| used) | 3 | 86 | 2 | 2 | 2 | 3 | 4 | 6 | 6 | 7 | 7 | 7 | 7 | 8.14 |
| | 4 | 90 | 2 | 3 | 3 | 3 | 3 | 4 | 5 | 5 | 5 | 5 | 5 | 5.56 |
| Total | | 336 | 5 | 7 | 8 | 10 | 13 | 17 | 19 | 21 | 21 | 23 | 25 | |

TABLE VI-continued

House Flies Repelled At Five Minute Time Intervals
20 Minutes Post Exposure

| Sample | Replicate | Number of House Flies | Cumulative Number of House Flies Repelled at Indicated Minutes | | | | | | | | | | | Overall Percent |
|---|---|---|---|---|---|---|---|---|---|---|---|---|---|---|
| | | | 10 | 15 | 20 | 25 | 30 | 35 | 40 | 45 | 50 | 55 | 60 | |
| Average Percent | | | 1 | 2 | 2 | 3 | 4 | 5 | 6 | 6 | 6 | 7 | 7 | 7.44 |
| A | 1 | 108 | 2 | 5 | 7 | 8 | 8 | 8 | 8 | 10 | 10 | 10 | 12 | 11.11 |
| | 2 | 95 | 0 | 5 | 5 | 6 | 7 | 7 | 9 | 11 | 12 | 12 | 16 | 16.84 |
| | 3 | 86 | 3 | 6 | 8 | 8 | 10 | 10 | 11 | 11 | 12 | 12 | 13 | 15.12 |
| | 4 | 96 | 2 | 3 | 5 | 6 | 9 | 11 | 11 | 14 | 16 | 17 | 17 | 17.71 |
| Total | | 385 | 7 | 19 | 25 | 28 | 34 | 36 | 39 | 46 | 50 | 51 | 58 | |
| Average Percent | | | 2 | 5 | 6 | 7 | 9 | 9 | 10 | 12 | 13 | 13 | 15 | 15.06 |
| B | 1 | 80 | 4 | 5 | 7 | 7 | 8 | 8 | 9 | 9 | 9 | 10 | 11 | 13.75 |
| | 2 | 100 | 2 | 4 | 5 | 6 | 7 | 10 | 11 | 11 | 11 | 12 | 12 | 12.00 |
| | 3 | 87 | 2 | 2 | 3 | 4 | 5 | 5 | 6 | 6 | 6 | 6 | 7 | 8.04 |
| | 4 | 91 | 2 | 4 | 5 | 6 | 6 | 6 | 7 | 7 | 7 | 9 | 10 | 10.99 |
| Total | | 358 | 10 | 15 | 20 | 23 | 26 | 29 | 33 | 33 | 33 | 37 | 41 | |
| Average Percent | | | 3 | 4 | 6 | 6 | 7 | 8 | 9 | 9 | 9 | 10 | 11 | 11.45 |
| C | 1 | 79 | 6 | 8 | 8 | 8 | 8 | 8 | 8 | 8 | 8 | 9 | 10 | 12.66 |
| | 2 | 86 | 3 | 5 | 5 | 6 | 6 | 6 | 6 | 6 | 7 | 7 | 8 | 9.30 |
| | 3 | 92 | 2 | 4 | 4 | 5 | 7 | 7 | 7 | 7 | 7 | 7 | 8 | 8.70 |
| | 4 | 91 | 0 | 1 | 1 | 2 | 2 | 2 | 4 | 6 | 7 | 7 | 9 | 9.89 |
| Total | | 348 | 11 | 18 | 18 | 11 | 23 | 23 | 25 | 27 | 29 | 30 | 35 | |
| Average Percent | | | 3 | 5 | 5 | 6 | 7 | 7 | 7 | 8 | 8 | 9 | 10 | 10.06 |

The results of this experiment show that the candle containing the bisabolene isomer mixture (2.5% of the total weight) is about 40% more efficacious from an insect repellency standpoint than a candle containing 10% citronella oil . . . and in addition, such candles containing the bisabolene isomer composition on burning yield an aesthetically pleasing scent which is totally unlike the 10% citronella oil-containing candle which yields an aesthetically displeasing scent.

What is claimed is:

1. A method of repelling at least one of the insect species:

(a) *Musca Domestica* L.(Diptera:Muscidae); and/or
(b) *Aedes aegypti* from a three dimensional space inhabited by at least one of said insect species comprising the step of exposing said three dimensional space inhabited by at least one of said insect species to a:

(a) *Musca domestica* L.(Diptera:Muscidae); and/or
(b) *Aedes aegypti* repelling concentration and quantity of an insect repellent composition of matter consisting essentially of bisabolene isomers defined according to the structure:

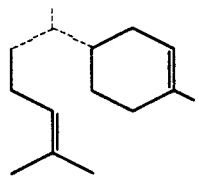

wherein in the mixture in each of the compound one of the dashed lines represents a carbon-carbon double bond and each of the other of the dashed lines represents a carbon-carbon single bond.

2. A method of repelling at least one of the insect species:

(a) *Musca domestica* L.(Diptera:Muscidae); and/or
(b) *Aedes aegypti* from a three dimensional space inhabited by at least one of said insect species comprising the step of exposing said three dimensional space inhabited by at least one of said insect species to a:

(a) *Musca domestica* L.(Diptera:Muscidae); and/or
(b) *Aedes aegypti* repelling concentration and quantity of an inspect repellent composition of matter consisting essentially of a bisabolene isomer containing composition prepared by treating nerolidol defined according to the structure:

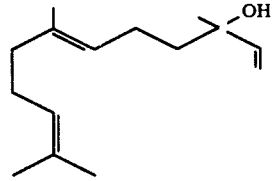

with a catalyst selected from the group consisting of phosphoric acid and citric acid and heating the composition in the presence of a solvent at a temperature of from 155° up to 175° C. for a period of time such that a majority of isomers is prepared defined according to the structure:

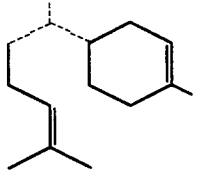

and, in addition, a minority of a mixture is prepared comprising compounds having the structures:

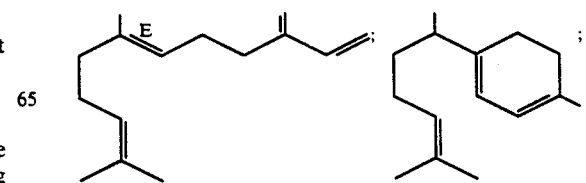

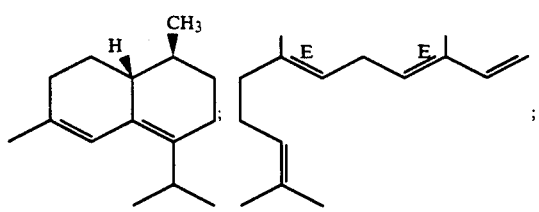

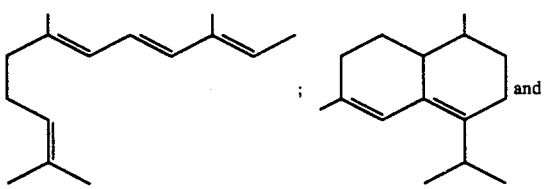

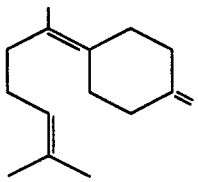

wherein the mixture of compounds defined according to the structure:

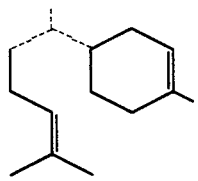

one of the dashed lines represents a carbon-carbon double bond and each of the other of the dashed lines represents carbon-carbon single bonds and fractionally distilling the resulting product at a temperature in the range of 109°–124° C. and a pressure in the range of 2.8–3.20 mm/Hg.

3. An insect repellent candle comprising a wick being surrounded by a cylindrical candle body, said candle body comprising a candle base and intimately admixed therewith a isabolene isomer containing composition consisting essentially of a mixture of bisabolene isomers defined according to the structure:

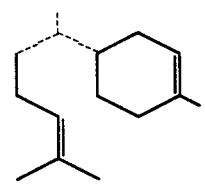

wherein, in the mixture of compounds defined according to the structure:

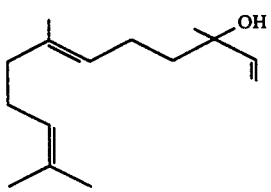

one of the dashed lines represents a carbon-carbon double bond and each of the other of the dashed lines represent carbon-carbon single bonds.

4. An insect repellent candle comprising a wick being surrounded by a cylindrical candle body, said candle body comprising a candle base and intimately admixed therewith a bisabolene isomer containing composition consisting essentially of a product prepared by treating nerolidol defined according to the structure:

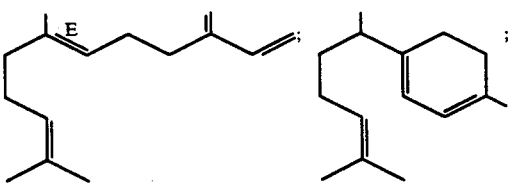

with a catalyst selected from the group consisting of phosphoric acid and citric acid and heating the composition in the presence of a solvent at a temperature of from 155° up to 175° C. for a period of time such that a majority of isomers is prepared defined according to the structure:

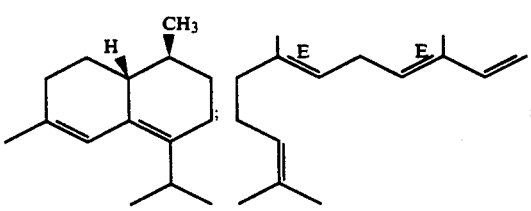

and in addition, a minority of a mixture is prepared comprising compound having the structures:

-continued
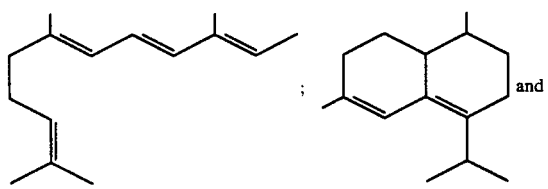
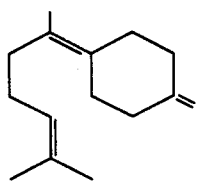
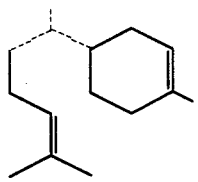
wherein, in the mixture of compounds defined according to the structure:
one of the dashed lines represents a carbon-carbon double bond and each of the other of the dashed lines represent carbon-carbon single bonds, and fractionally distilling the resulting product at a temperature in the range of 109°–124° C. and a pressure in the range of 2.8–3.20 mm/Hg.
* * * * *